(12) United States Patent
Hioki et al.

(10) Patent No.: US 12,336,717 B2
(45) Date of Patent: Jun. 24, 2025

(54) HEMOSTATIC DEVICE

(71) Applicant: TERUMO KABUSHIKI KAISHA, Tokyo (JP)

(72) Inventors: Yuichi Hioki, Fuji Shizuoka (JP); Satoshi Wada, Fujinomiya Shizuoka (JP); Ryo Okamura, Fujinomiya Shizuoka (JP); Masako Miyashita, Fujinomiya Shizuoka (JP); Fumi Watanabe, Hadano Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1114 days.

(21) Appl. No.: 17/192,386

(22) Filed: Mar. 4, 2021

(65) Prior Publication Data

US 2021/0186520 A1    Jun. 24, 2021

Related U.S. Application Data

(63) Continuation of application No. PCT/JP2019/035028, filed on Sep. 5, 2019.

(30) Foreign Application Priority Data

Sep. 6, 2018   (JP) ................. 2018-166587

(51) Int. Cl.
*A61F 13/00*   (2024.01)
*A61B 17/12*   (2006.01)
(Continued)

(52) U.S. Cl.
CPC ............ *A61B 17/135* (2013.01); *A61B 90/08* (2016.02); *A61B 2017/00544* (2013.01);
(Continued)

(58) Field of Classification Search
None
See application file for complete search history.

(56) References Cited

U.S. PATENT DOCUMENTS

2004/0098035 A1   5/2004   Wada et al.
2015/0335334 A1   11/2015  Pancholy et al.

FOREIGN PATENT DOCUMENTS

JP   2008119517 A  *  5/2008   ......... A61B 17/1325
JP   2018522706 A      8/2018

OTHER PUBLICATIONS

JP-2008119517-A translation (Year: 2008).*

(Continued)

*Primary Examiner* — Kim M Lewis
(74) *Attorney, Agent, or Firm* — Kim & Stewart LLP

(57) ABSTRACT

A hemostatic device includes a covering member configured to cover a site where bleeding is to be stopped on a hand of a patient, a securing member configured to secure the covering member to the hand, an inflatable member connected to the covering member and inflatable by a fluid, and an auxiliary member having a smaller outer shape than the inflatable member. The covering member includes a body, a first arm protruding from a first side of the body, and a second arm protruding from a second side facing the first side. The body includes a first end portion located on a distal side of the body and a second end portion located on a proximal side thereof. The inflatable member is connected to the second end portion, and the auxiliary member is connected to the first end portion and is interposed between the body and the inflatable member.

20 Claims, 14 Drawing Sheets

(51) Int. Cl.
  *A61B 17/135* (2006.01)
  *A61B 90/00* (2016.01)
  *A61B 17/00* (2006.01)

(52) U.S. Cl.
  CPC ............... *A61B 2017/00557* (2013.01); *A61B 2017/00862* (2013.01); *A61B 2090/0807* (2016.02)

(56) References Cited

OTHER PUBLICATIONS

English Translation of International Search Report dated Oct. 29, 2019, mailed in counterpart International Application No. PCT/JP2019/035028, 1 page.
English Translation of Written Opinion dated Oct. 29, 2019, mailed in counterpart International Application No. PCT/JP2019/035028, 5 pages.

* cited by examiner

HEMOSTATIC DEVICE

CROSS-REFERENCE TO RELATED APPLICATION(S)

This application is a continuation of International Patent Application No. PCT/JP2019/035028, filed on Sep. 5, 2019, which is based upon and claims the benefit of priority from Japanese Patent Application No. 2018-166587 filed on Sep. 6, 2018, the entire contents of which are incorporated herein by reference.

BACKGROUND OF THE INVENTION

Field of the Invention

Embodiments described herein generally relate to a hemostatic device.

Background Art

In a known catheter procedure, a blood vessel in an arm of a patient (for example, radial artery) is punctured and various medical elongated bodies are introduced into the blood vessel via the puncture site for treatment or therapy on a lesion area. The catheter procedure utilizing the radial artery is referred to as transradial artery approach and is considered a useful technique for, for example, coronary artery access and lower limb artery access.

A radial artery located in an arm of a human body is connected to a palmar artery which bypasses a hand side. Therefore, currently, as a new method of transradial artery approach, a catheter procedure using distal transradial approach (dTRA) has been attempted to access the palmar artery including a distal radial artery from an anatomical snuffbox located on a dorsal side of the hand or from a position around the snuffbox, and perform treatment through the vascular access site.

Blood vessels such as palmar arteries located in the hand are located in places where there are many movable parts such as fingers. For this reason, when an operator punctures a blood vessel such as a palmar artery and forms a puncture site on a surface of a hand, a shape around the puncture site of the hand changes depending on the movement of the hand. Therefore, when hemostasis is performed at the puncture site, a pressing member placed on the hand is preferably an inflatable member that follows the movement of the hand and easily adjusts a compressive force on the puncture site.

However, when the pressing member is the inflatable member, the inflatable member exerts a force to inflate from the inside to the outside of the inflatable member in an inflated state. For this reason, in a hemostatic device having the inflatable member, a shape around a hemostatic site changes due to the movement of the hand, the inflatable member shifts from the puncture site, and a compressive force of the inflatable member on the puncture site may not be properly maintained. Therefore, when hemostasis is performed at the puncture site of the hand, the hemostatic device having the inflatable member needs to suppress misalignment of the inflatable member due to the force acting in a direction away from the puncture site, thereby appropriately securing the inflatable member to the puncture site. In this way, it is considered that the hemostatic device having the inflatable member can appropriately maintain the compressive force of the inflatable member on the puncture site even when the shape around the puncture site is changed by the movement of the hand.

In addition, when the pressing member is the inflatable member, it is possible to increase the compressive force on the hand by inflating the inflatable member. For this reason, it is considered that the misalignment of the inflatable member from the puncture site on the hand can be suppressed by adjusting the degree of inflation of the inflatable member. However, when the inflatable member is inflated, if an edge portion of the inflatable member (e.g., an outer peripheral edge) is strongly pressed against the hand, the patient may feel pain.

SUMMARY OF THE INVENTION

One or more embodiments provide a hemostatic device capable of suppressing misalignment of an inflatable member with respect to a site where bleeding is to be stopped on the hand even when the patient moves the hand in a state where the inflatable member is inflated. Additionally, the hemostatic device is further capable of reducing pain felt by the patient when an edge portion of the inflatable member in the inflated state is pressed against the hand.

A hemostatic device according to one or more embodiments is attachable to a hand of a patient and includes a covering member configured to cover a site where bleeding is to be stopped on a hand of a patient, a securing member configured to secure the covering member to the hand when the covering member covers the site, an inflatable member connected to the covering member and inflatable by injection of a fluid, and a deformable auxiliary member having a smaller outer shape than an outer shape of the inflatable member. The covering member includes a main body, a first arm portion protruding from a first side of the main body, and a second arm portion protruding from a second side of the main body, wherein the first and second sides are opposite sides of the main body. The main body includes a first end portion located on a distal side of the main body between the first arm portion and the second arm portion, and a second end portion located on a proximal side of the main body between the first arm portion and the second arm portion. The inflatable member is connected to the second end portion, and the auxiliary member is connected to the first end portion and is interposed between the main body and the inflatable member.

DETAILED DESCRIPTION OF THE INVENTION

Hereinafter, one or more embodiments of the invention will be described with reference to the accompanying drawings. The following description does not limit the technical scope or the meaning of terms described in the appended claims. In addition, the dimensions or scales on the drawings may be different from actual ones.

FIGS. 1 to 7 are diagrams illustrating a hemostatic device 100 according to an embodiment, and FIGS. 8 to 12 are diagrams illustrating usage examples of the hemostatic device 100.

Figure 9:
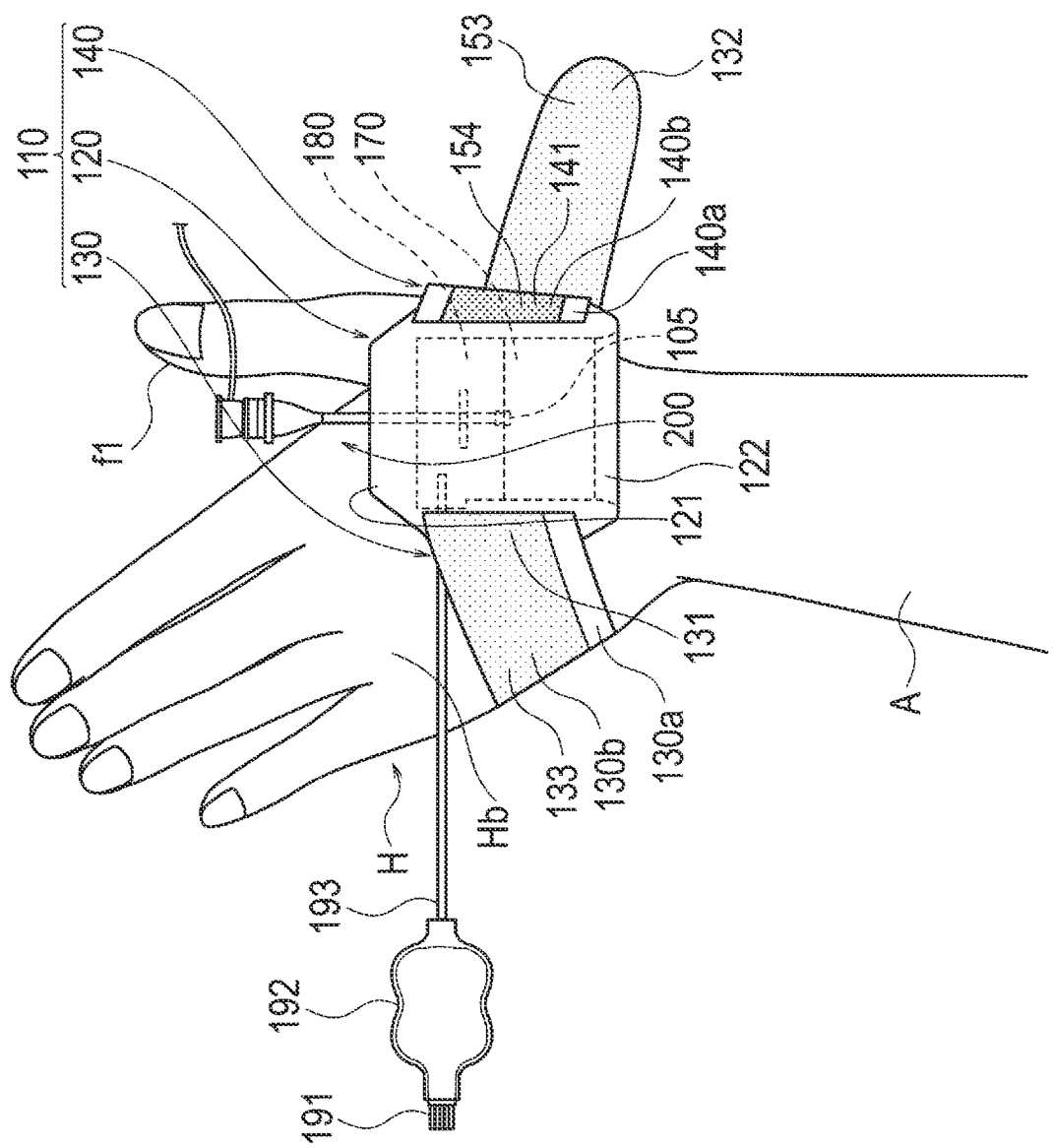
FIG. 9 is a diagram schematically illustrating a usage example of the hemostatic device.
Figure 10:
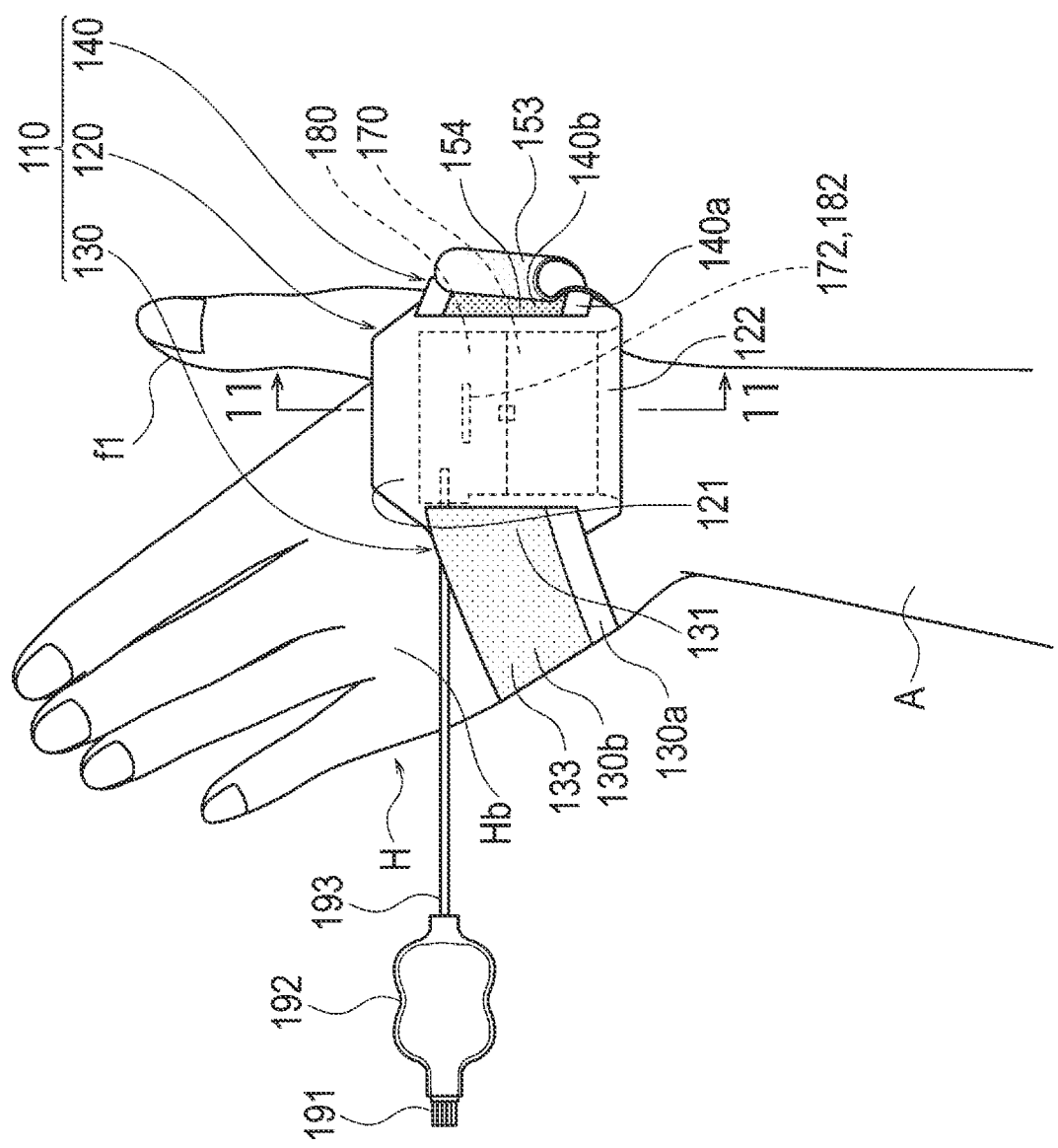
FIG. 10 is a diagram schematically illustrating a usage example of the hemostatic device.
Figure 11:
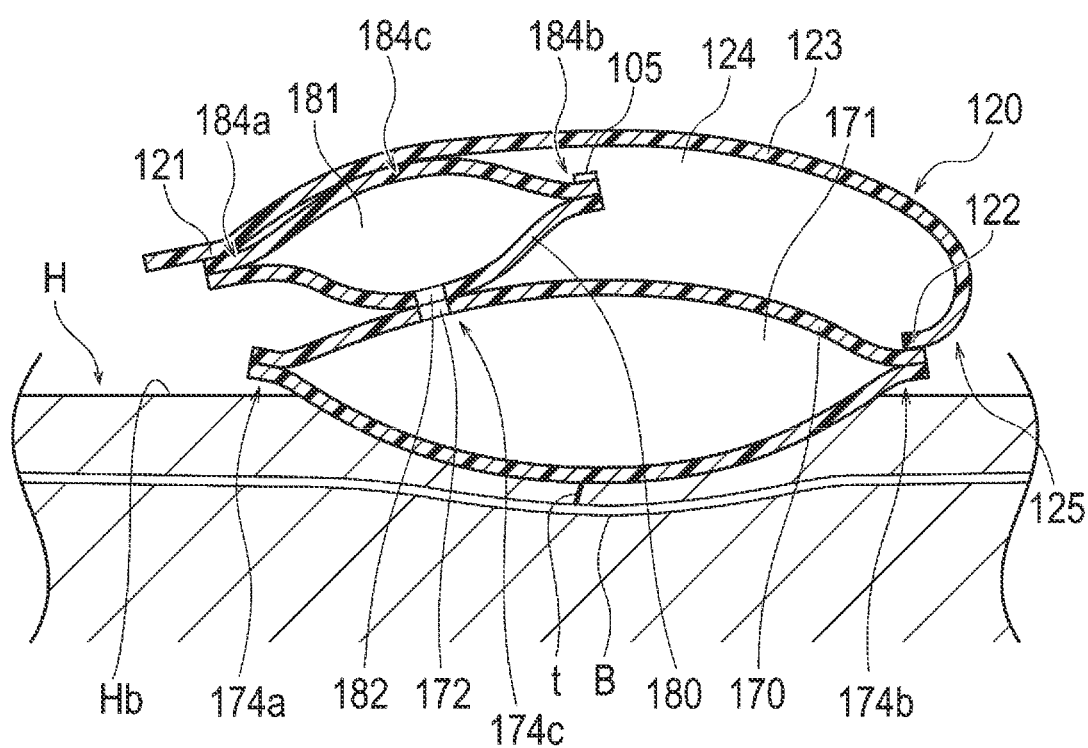
FIG. 11 is a diagram schematically illustrating a part of a cross section taken along arrow 11-11 illustrated in FIG. 10.

For example, as illustrated in FIGS. 9, 10, and 11, when removing a sheath tube of an introducer 200 indwelling at a puncture site t where bleeding is to be stopped formed on a radial artery side (for example, an artery around an anatomical snuffbox or a distal radial artery running on a fingertip side of the snuffbox) of a deep palmar artery B running on a side of a dorsal side Hb of a hand (for example, left hand) H located on the fingertip side of a forearm A of a patient, the hemostatic device 100 can be used to perform hemostasis on the puncture site t. The anatomical snuffbox is a cavity in the hand located on the radial side of the forearm A when the patient spreads a thumb f1 of the hand H.

In brief, as illustrated in FIGS. 1, 2, 10, and 11, the hemostatic device 100 includes a covering member 110 to cover the puncture site t on the hand H of the patient, a plurality of securing members 151, 152, 153, 154, and 155 for securing the covering member 110 while the covering member 110 covers the puncture site t, an inflatable member 170 connected to the covering member 110 and inflated by injection of a fluid, and an auxiliary member 180 which has a smaller outer shape than that of the inflatable member 170 and is deformable.

Figure 1:
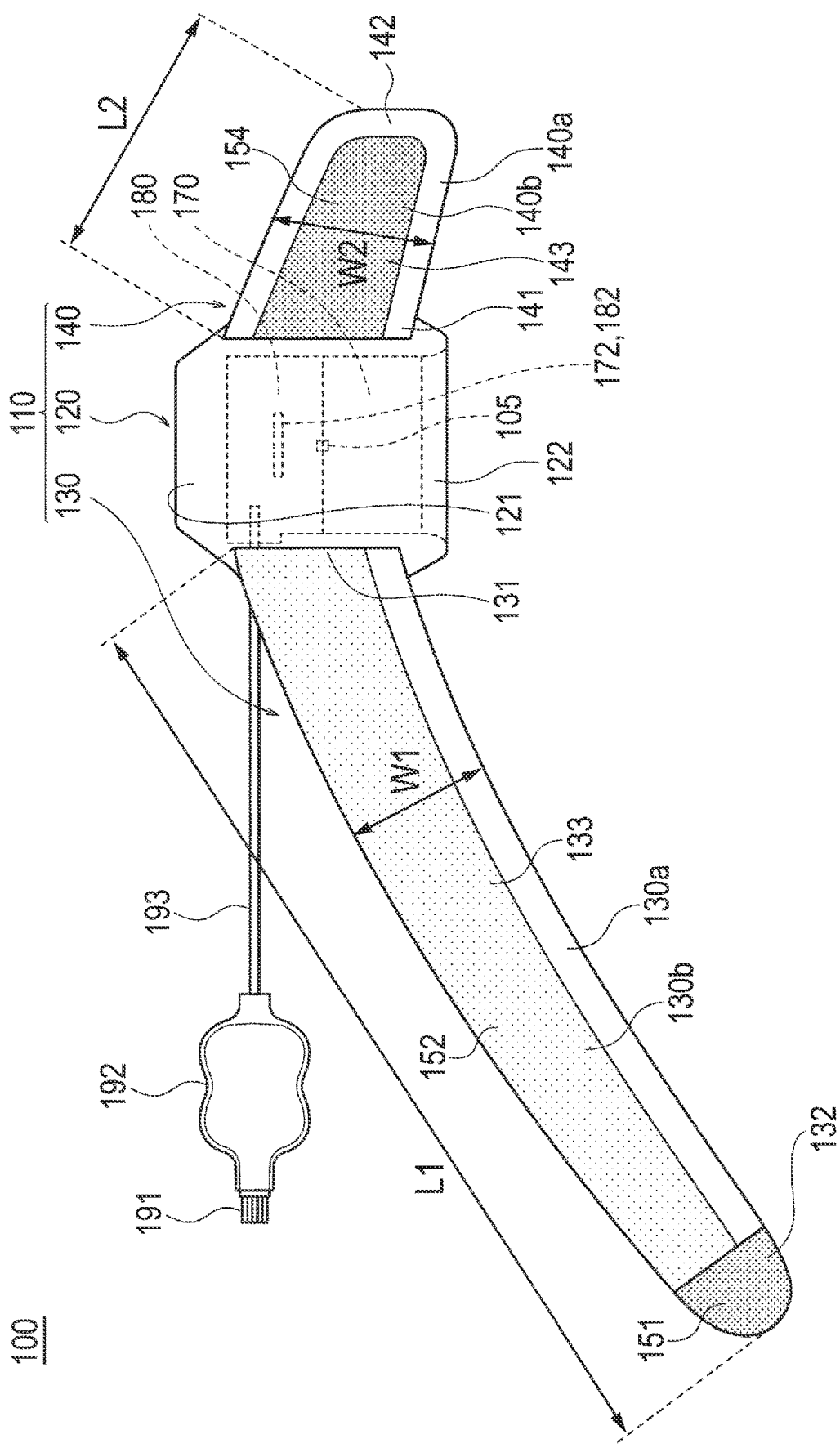
FIG. 1 is a plan view of a hemostatic device according to an embodiment, seen from an outer surface side of a main body of a covering member.
Figure 2:
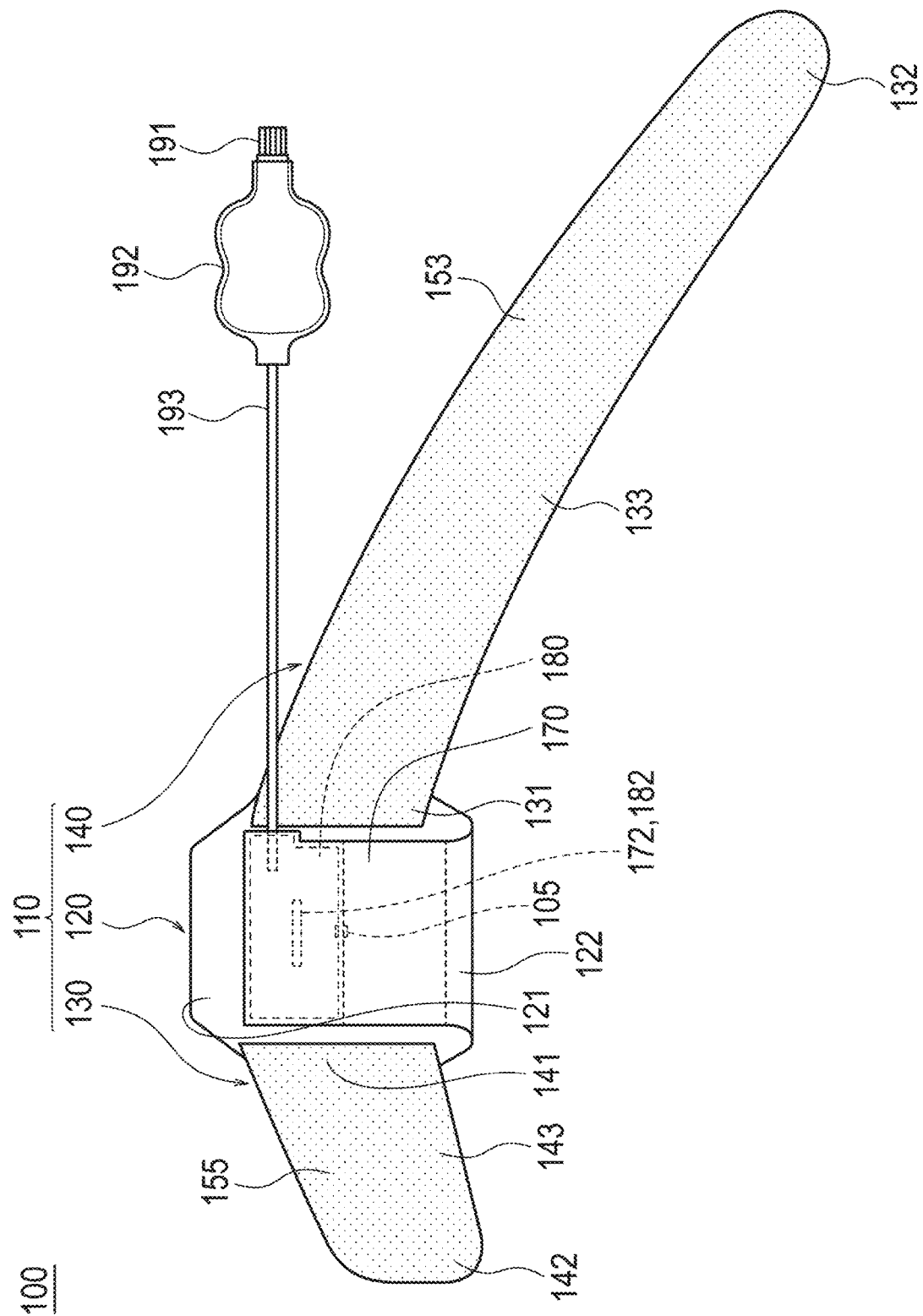
FIG. 2 is a plan view of the hemostatic device, seen from an inner surface side of the main body of the covering member.

FIG. 1 illustrates a plan view of the hemostatic device 100 seen from an outer surface side of a main body 120 of the covering member 110, and FIG. 2 illustrates a plan view of the hemostatic device 100 seen from an inner surface side of the main body 120 of the covering member 110. An "inner surface" of the main body 120 is a surface on a side to which the inflatable member 170 disposed to face a body surface of the patient when the hemostatic device 100 is worn on the patient is connected, and an "outer surface" of the main body 120 is a surface opposite to the inner surface. In addition, a "distal side" used in the following description refers to a side where a fingertip of the hand H is disposed in a state where the hemostatic device 100 is worn on the hand H of the patient (i.e., the upper side in FIG. 1 and FIG. 3, and the left side in FIG. 5), and a "proximal side" is opposite to the distal side, closer to the wrist than the fingertip of the hand. In the following description, a state where arm portions 130 and 140 of the covering member 110 are extended without being attached to the hand H of the patient will be referred to as a "non-worn state".

<Covering Member>

As illustrated in FIGS. 1 and 2, the covering member 110 includes the main body 120 to which the inflatable member 170 is connected, the first arm portion 130 protruding from the main body 120, and the second arm portion 140 protruding from a position facing the first arm portion 130 with the main body 120 interposed therebetween.

<Main Body>

Figure 5:
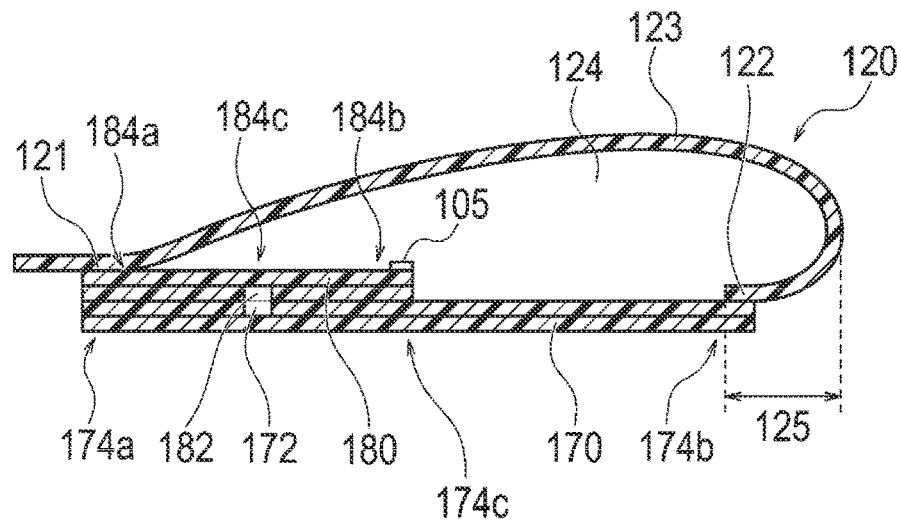
FIG. 5 is a cross-sectional view of the hemostatic device taken along arrow 5-5 illustrated in FIG. 3.

As illustrated in FIGS. 1 and 5, the main body 120 includes a first end portion 121 located on a distal side of the main body 120 between the first arm portion 130 and the second arm portion 140, a second end portion 122 located on a proximal side of the main body 120 between the first arm portion 130 and the second arm portion 140, and an extending portion 123 which extends between the first end portion 121 and second end portion 122.

The main body 120 is made of a flexible member. A space 124 in which the inflatable member 170 and the auxiliary member 180 are disposed is formed inside the extending portion 123 of the main body 120. The space 124 communicates with the outside of the main body 120 along a direction intersecting an extending direction of the extending portion 123 (i.e., the direction along which the arm portions 130 and 140 protrude).

As illustrated in FIG. 5, a curved region 125 is formed on the second end portion 122 side of the main body 120. The curved region 125 is a part of the extending portion 123. The curved region 125 is adjacent to the second end portion 122 and has a cross-sectional shape convexly protruding to the proximal side of the main body 120.

The second end portion 122 of the main body 120 extends continuously from the extending portion 123 and forms an end part of the extending portion 123 that curves toward the distal side of the main body 120. The first end portion 121 side of the extending portion 123 has a cross-sectional shape extending substantially linearly toward the first end portion 121.

The inflatable member 170 is connected to the second end portion 122 of the main body 120. In the inflatable member 170, a proximal portion 174b of the inflatable member 170, which is a peripheral edge located at an end portion of the inflatable member 170 on the proximal side, is connected to the second end portion 122 of the main body 120.

Figure 13:
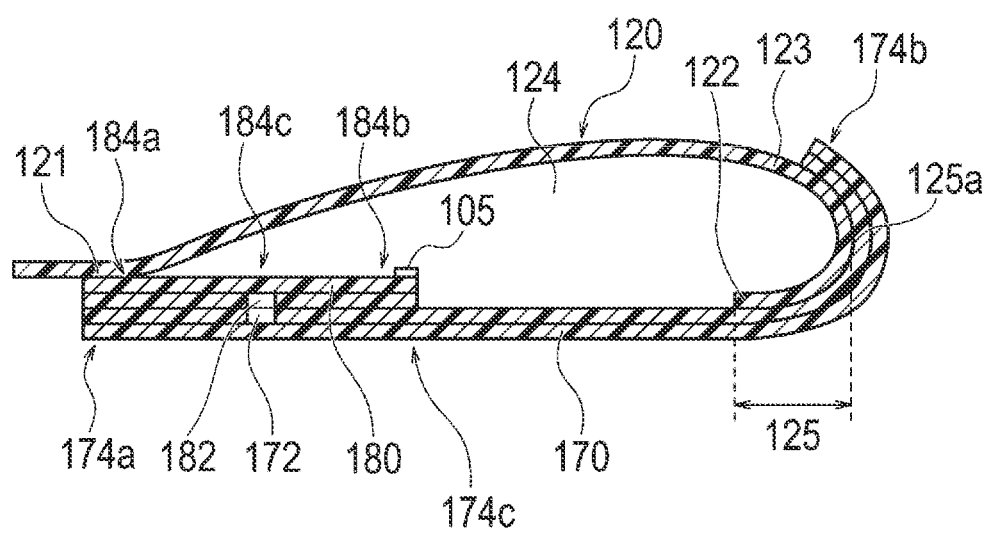
FIG. 13 is a cross-sectional view of a modified connection position of the covering member of the inflatable member.

As illustrated in FIG. 13, the inflatable member 170 may be connected from the second end portion 122 of the main body 120 to the curved region 125 of the extending portion 123. In this instance, the proximal portion 174b of the inflatable member 170 is preferably located on the first end portion 121 side of an apex 125a of a convex portion protruding toward the proximal side of the main body 120 of the curved region 125. In this way, the proximal portion 174b of the inflatable member 170 is located on the outer surface side of the main body 120 in a state where the hemostatic device 100 is worn on the hand H of the patient. For this reason, even when the patient moves the hand H in a state where the inflatable member 170 is inflated, it is possible to reliably prevent the proximal portion 174b of the inflatable member 170, which is the edge portion of the inflatable member 170 on the proximal side, from biting into the hand. Therefore, in a case where the hemostatic device 100 has the inflatable member 170 and the main body 120 of the covering member 110 connected to each other as illustrated in FIG. 13, it is possible to reduce the pain of the patient during hemostasis.

The auxiliary member 180 is connected to the first end portion 121 of the main body 120. The auxiliary member 180 is connected to the first end portion 121 in a state of being interposed between the main body 120 and the inflatable member 170. In the auxiliary member 180, a distal portion 184a of the auxiliary member 180, which is a peripheral edge located at an end portion of the auxiliary member 180 on the distal side, is connected to the first end portion 121 of the main body 120.

The auxiliary member 180 is connected to the inflatable member 170 at a position biased to one end side (i.e., the distal portion 174a side) of the inflatable member 170. In an embodiment, the inflatable member 170 and the auxiliary member 180 are connected to each other at a center portion 184c of the auxiliary member 180. The center portion 184c is located at a center position of the auxiliary member 180 in a right-left direction illustrated in FIG. 5.

As described above, the distal portion 184a of the auxiliary member 180 is connected to the first end portion 121 of the main body 120 of the covering member 110, and the proximal portion 174b of the auxiliary member 180 is connected to the second end portion 122 of the main body of the covering member 110. The inflatable member 170 and the auxiliary member 180 are connected to each other at the center portion 184c of the auxiliary member 180. Therefore, in the covering member 110, only the first and second end portions 121 and 122 of the main body 120 are directly connected to the inflatable member 170 and the auxiliary member 180.

In the main body 120, a portion overlapping a marker portion 105 described later in the plan view of FIGS. 1 and 3 and surroundings thereof in the main body 120 are preferably transparent (including colored transparent, colorless transparent, and translucent). By adopting the above configuration, the operator can visually recognize the puncture site t from the outer surface side of the main body 120 even when the marker portion 105 is superposed on the puncture site t.

<First Arm Portion and Second Arm Portion>

In the following description, a longitudinal direction of the first arm portion 130 means a horizontal direction in FIGS. 1 and 2 along which the first arm portion 130 extends in the non-worn state. In addition, a width direction of the first arm portion 130 is a direction intersecting the longitudinal direction of the first arm portion 130 on the plan views illustrated in FIGS. 1 and 2. Similarly, a longitudinal direction of the second arm portion 140 is the horizontal direction of FIGS. 1 and 2 along which the second arm portion 140 extends in the non-worn state, and a width direction of the second arm portion 140 is a direction intersecting the longitudinal direction of the second arm portion 140 on the plan views illustrated in FIGS. 1 and 2.

As illustrated in FIGS. 1 and 2, the first arm portion 130 has a first region 131 connected to the main body 120, a second region 132 located at an end portion opposite to a side where the first region 131 is disposed, and a main body region 133 located between the first region 131 and the second region 132.

The first arm portion 130 is formed of a flexible band-shaped member that can be wrapped around the hand H of the patient.

The main body region 133 of the first arm portion 130 is curved so that the second region 132 side is separated from the main body 120 in the non-worn state.

As illustrated in FIG. 1, the first securing member 151 is disposed on an outer surface of the second region 132 of the first arm portion 130. The second securing member 152 is disposed on a part of an outer surface of the main body region 133 of the first arm portion 130. As illustrated in FIG. 2, the third securing member 153 is disposed on an inner surface of each of the regions 131, 132, and 133 of the first arm portion 130.

Figure 7:
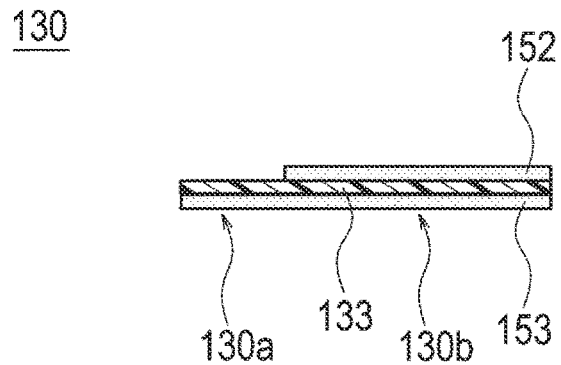
FIG. 7 is a cross-sectional view of a first arm portion taken along arrow 7-7 illustrated in FIG. 4.

FIG. 7 illustrates a cross-sectional view of a peripheral edge 130a on the proximal side of the main body region 133 of the first arm portion 130 and a center portion 130b passing through a center of the first arm portion 130 along the width direction.

As illustrated in FIGS. 1, 2, and 7, a member forming the main body region 133 of the first arm portion 130 and the third securing member 153 disposed on the inner surface of the main body region 133 are disposed to overlap each other at the peripheral edge 130a of the main body region 133 of the first arm portion 130 on the proximal side. Meanwhile, a member forming the main body region 133 of the first arm portion 130, the second securing member 152 disposed on the outer surface of the main body region 133, and the third securing member 153 disposed on the inner surface of the main body region 133 are disposed to overlap each other at the center portion 130b of the main body region 133 of the first arm portion 130. For this reason, in the first arm portion 130, when the peripheral edge 130a on the proximal side of the main body region 133 and the center portion 130b are compared to each other, a wall thickness of the peripheral edge 130a on the proximal side of the main body region 133 (i.e., the vertical dimension of FIG. 7) is smaller than a wall thickness of the center portion 130b.

As illustrated in FIGS. 1 and 2, the second arm portion 140 has a first region 141 connected to the main body 120, a second region 142 located at an end portion opposite to a side where the first region 141 is disposed, and a main body region 143 located between the first region 141 and the second region 142.

The second arm portion 140 is formed of a flexible member that can be deformed along a shape of an external surface of the hand H of the patient.

The main body region 143 of the second arm portion 140 is curved so that the second region 142 side is separated from the main body 120 in the non-worn state.

As illustrated in FIG. 1, the fourth securing member 154 is disposed on a part of the outer surface of the first region 141 and the main body region 143 of the second arm portion 140. As illustrated in FIG. 2, the fifth securing member 155 is disposed on the inner surface of each of the regions 141, 142, and 143 of the second arm portion 140.

Figure 6:
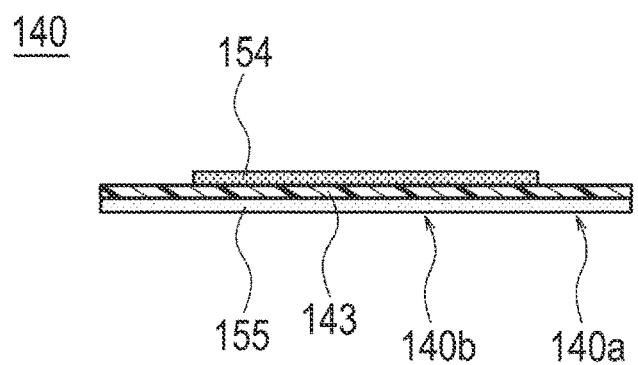
FIG. 6 is a cross-sectional view of a second arm portion taken along arrow 6-6 illustrated in FIG. 3.

FIG. 6 illustrates a cross-sectional view of a peripheral edge 140a on the proximal side of the main body region 143 of the second arm portion 140 and a center portion 140b passing through a center of the second arm portion 140 in the width direction.

As illustrated in FIGS. 1, 2, and 6, a member forming the main body region 143 of the second arm portion 140 and the fifth securing member 155 disposed on the inner surface of the main body region 143 are disposed to overlap each other at the peripheral edge 140a of the main body region 143 of the second arm portion 140 on the proximal side. Meanwhile, a member forming the main body region 143 of the second arm portion 140, the fourth securing member 154 disposed on the outer surface of the main body region 143, and the fifth securing member 155 disposed on the inner surface of the main body region 143 are disposed to overlap each other at the center portion 140b of the main body region 143 of the second arm portion 140. For this reason, in the second arm portion 140, when the peripheral edge 140a on the proximal side of the main body region 143 and the center portion 140b are compared to each other, a wall thickness of the peripheral edge 140a on the proximal side of the main body region 143 (i.e., the vertical dimension of FIG. 6) is smaller than a wall thickness of the center portion 140b.

Figure 3:
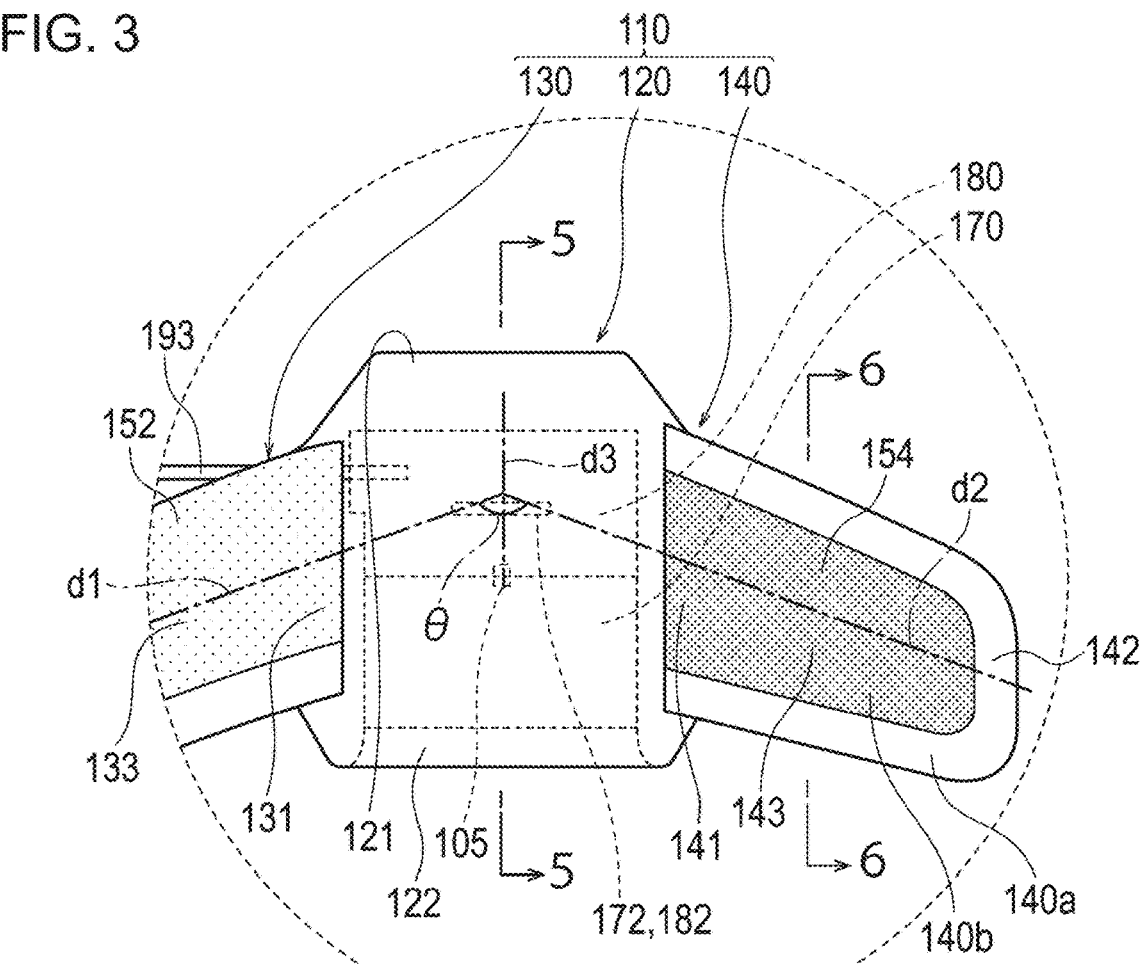
FIG. 3 is an enlarged plan view illustrating a part of the covering member.
Figure 4:
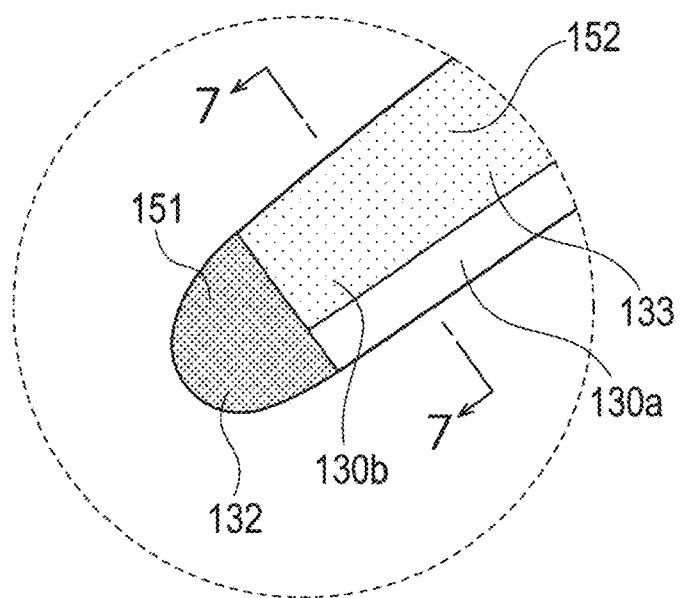
FIG. 4 is an enlarged plan view illustrating a part of a first arm portion of the covering member.

As illustrated in FIG. 3, the second arm portion 140 protrudes from the main body 120 while forming an obtuse angle θ with the longitudinal direction of the first arm portion 130. The obtuse angle θ formed between the first arm portion 130 and the second arm portion 140 is an angle at which a straight line d1 extending along the center portion 130b of the main body region 133 of the first arm portion 130 and a straight line d2 extending along the center portion 140b of the main body region 143 of the second arm portion 140 intersect on the main body 120. For example, the obtuse angle θ can be set to 120° to 170°.

As described above, in the hemostatic device 100, the first arm portion 130 and the second arm portion 140 form the obtuse angle θ in the plan views illustrated in FIGS. 1 and 3. For this reason, the first arm portion 130 is inclined and extends toward the second end portion 122 side so as to be separated from the first end portion 121 side of the main body 120. Similarly, the second arm portion 140 is inclined and extends toward the second end portion 122 side in a direction away from the first end portion 121 side of the main body 120. Therefore, the first arm portion 130 and the second arm portion 140 extend from the first end portion 121 of the main body 120 toward the second end portion 122 side so as to spread in an inverted V-shape without intersecting each other.

In the hemostatic device 100, since the second arm portion 140 forms the obtuse angle θ with the longitudinal direction of the first arm portion 130, the first arm portion 130 and the second arm portion 140 can be connected in a state of being extended toward a wrist side of the hand H of the patient (see FIG. 10). For this reason, the first arm portion 130 and the second arm portion 140 can be secured on the wrist side where a movable range is small, and a movable range on the fingertip side of the hand H can be maintained. In addition, the inflatable member 170 can apply a strong compressive force to the proximal side of the inflatable member 170 (i.e., the wrist side) by securing the first arm portion 130 and the second arm portion 140. Further, the inflatable member 170 can apply a strong compressive force to the distal side of the inflatable member 170 by the auxiliary member 180. For this reason, the hemostatic device 100 can appropriately apply the compressive force of the inflatable member 170 to the hand H of the patient.

An angle formed by a straight line d3 (see FIG. 3) passing through a center position of the main body 120 and the straight line d1 along the longitudinal direction of the first arm portion 130 and an angle formed by the straight line d3 and the straight line d2 along the longitudinal direction of the second arm portion 140 may or may not be the same.

As illustrated in FIG. 1, the first arm portion 130 is formed longer than the second arm portion 140. As illustrated in FIG. 1, a magnitude relationship between a length L1 of the first arm portion 130 and a length L2 of the second arm portion 140 may be defined by the linear distances L1 and L2 of the arm portions 130 and 140 in the non-worn state. The length L1 of the first arm portion 130 can be set to, for example, 150 mm to 400 mm, and the length L2 of the second arm portion 140 can be set to, for example, 40 mm to 400 mm.

For example, a width W1 of the first arm portion 130 can be set to be smaller than a width W2 of the second arm portion 140. The width W1 of the first arm portion 130 can be defined by a maximum value of a width of the first arm portion 130 when the width of the first arm portion 130 changes in the longitudinal direction. Further, the width W2 of the second arm portion 140 can be defined by a maximum value of a width of the second arm portion 140 when the width of the second arm portion 140 changes in the longitudinal direction. The width W1 of the first arm portion 130 can be set to, for example, 10 mm to 30 mm, and the width W2 of the second arm portion 140 can be set to, for example, 15 mm to 45 mm.

In an embodiment, in the covering member 110, the main body 120 and the arm portions 130 and 140 are formed of separate members. The main body 120 and the first arm portion 130, and the main body 120 and the second arm portion 140 can be connected by, for example, adhesion, welding, etc. However, in the hemostatic device 100, any part of the main body 120, the first arm portion 130, and the second arm portion 140 in the covering member 110 may be integrally formed of one member.

The main body 120 is preferably made of a material having higher elasticity than that of the first arm portion 130 and the second arm portion 140. In this way, when the hemostatic device 100 is attached to the hand H of the patient, the arm portions 130 and 140 are wrapped around a limb of the patient, so that the main body 120 is extended by being pulled toward each of the first arm portion 130 side and the second arm portion 140 side. In this way, since the main body 120 is easily deformed due to changes in physical properties at each of boundaries between the main body 120 and the first arm portion 130 and between the main body 120 and the second arm portion 140, it is possible to easily dispose the first arm portion 130 and the second arm portion 140 on the hand H of the patient in a state where the main body 120 is disposed at the puncture site t formed on the hand H of the patient.

A material used for the main body 120 of the covering member 110 is not particularly limited. Examples thereof include polyvinyl chloride, polyolefin such as polyethylene, polypropylene, polybutadiene, or ethylene-vinyl acetate copolymer (EVA), polyester such as polyethylene terephthalate (PET) or polybutylene terephthalate (PBT), polyvinylidene chloride, silicone, polyurethane, various thermoplastic elastomers such polyamide elastomer, polyurethane elastomer, and polyester elastomer, nylon, nylon elastomer, or any combination thereof (e.g., blended resin, polymer alloy, laminate, etc.).

A material used for the first arm portion 130 and the second arm portion 140 of the covering member 110 is not particularly limited. Examples thereof may include the same materials as the materials exemplified as the main body 120 of the covering member 110, woven fabric, nonwoven fabric, felt, cloth, knitted fabric, and paper.

<Securing Member>

As illustrated in FIGS. 1 and 2, the hemostatic device 100 includes five securing members of the first securing member 151, the second securing member 152, the third securing member 153, the fourth securing member 154, and the fifth securing member 155.

As illustrated in FIG. 1, the first securing member 151 and the second securing member 152 are disposed on the outer surface of the first arm portion 130. The first securing member 151 is disposed in the second region 132 of the first arm portion 130. The second securing member 152 is disposed in a part of the first arm portion 130 excluding the first region 131 and the peripheral edge 130a on the proximal side of the main body region 133.

As illustrated in FIG. 1, the fourth securing member 154 is disposed on the outer surface of the second arm portion 140. The fourth securing member 154 is disposed in the first region 141 of the second arm portion 140 and the center portion 140b of the main body region 143.

As illustrated in FIG. 2, the third securing member 153 is disposed on the inner surface of the first arm portion 130. The third securing member 153 is disposed on the entire inner surface of the first arm portion 130.

As illustrated in FIG. 2, the fifth securing member 155 is disposed on the inner surface of the second arm portion 140. The fifth securing member 155 is disposed on the entire inner surface of the second arm portion 140.

The first securing member 151 and the fourth securing member 154 are configured as a male side of a surface fastener. The second securing member 152, the third securing member 153, and the fifth securing member 155 are configured as a female side of the surface fastener. The surface fastener is a fastener that is removable in terms of surface, and is, for example, MAGIC TAPE® or VEL-CRO®.

Specific configurations of the securing members 151, 152, 153, 154, and 155 are not limited as long as the first arm portion 130 wrapped around the limb of the patient can be secured to the second arm portion 140. For example, some of the securing members may be omitted, and positions where the securing members are disposed on the arm portions 130 and 140 may be changed as appropriate. Further, when each of the securing members 151, 152, 153, 154, and 155 includes the surface fastener, the male side and the female side of the surface fastener may be interchanged. Further, the securing members 151, 152, 153, 154, and 155 may be snaps, buttons, clips, frame members in which holes are formed, etc.

<Inflatable Member and Auxiliary Member>

As illustrated in FIGS. 3, 5, and 11, the auxiliary member 180 has an outer shape on the plan view smaller than that of the inflatable member 170. The auxiliary member 180 is disposed to overlap the inflatable member 170 on the distal side of the main body 120. FIG. 5 illustrates a cross section of the inflatable member 170 and the auxiliary member 180 in a state before inflation, and FIG. 11 illustrates a cross section of the inflatable member 170 and the auxiliary member 180 in a state after inflation.

As illustrated in FIG. 11, the inflatable member 170 has a lumen 171 into which a fluid can be injected, and a communication hole 172 formed at a position facing the auxiliary member 180.

In an embodiment, the auxiliary member 180 is an auxiliary inflatable portion that can be inflated by injection of a fluid.

The auxiliary member 180 has a lumen 181 into which a fluid can be injected, and a communication hole 182 formed at a position facing the communication hole 172 of the inflatable member 170.

The communication hole 182 of the auxiliary member 180 is disposed at the center portion 184c of the auxiliary member 180. The lumen 181 of the auxiliary member 180 communicates with the lumen 171 of the inflatable member 170 through the communication hole 182 of the auxiliary member 180 and the communication hole 172 of the inflatable member 170. The auxiliary member 180 is connected to the inflatable member 170 in a state of communicating with the inflatable member 170 through the communication holes 172 and 182.

In an embodiment, the inflatable member 170 has a substantially square shape on the plan view illustrated in FIG. 3. The auxiliary member 180 has a rectangular shape including a set of long sides having substantially the same length as that of one side of the inflatable member 170 and a set of short sides having approximately half the length of one side of the inflatable member 170. The long sides of the auxiliary member 180 are disposed along the right-left direction of FIG. 3 along which the arm portions 130 and 140 protrude from the main body 120.

As described above, the auxiliary member 180 is connected to the inflatable member 170 at a position biased toward one end side (i.e., the distal portion 174a side) of the inflatable member 170. For this reason, as illustrated in FIG. 5, the distal portion 184a of the auxiliary member 180 is disposed near the distal portion 174a of the inflatable member 170, the proximal portion 184b of the auxiliary member 180 is disposed near the center portion 174c of the inflatable member 170, and the center portion 184c of the auxiliary member 180 is disposed between the distal portion 174a and the center portion 174c of the inflatable member 170.

The inflatable member 170 is connected to the center portion 184c of the auxiliary member 180. Specifically, in the inflatable member 170, only a certain range around the communication hole 172 of the inflatable member 170 is secured to a periphery of the communication hole 182 located at the center portion 184c of the auxiliary member 180.

As illustrated in FIG. 3, the communication hole 172 of the inflatable member 170 and the communication hole 182 of the auxiliary member 180 extend along a longitudinal direction of the auxiliary member 180. In the hemostatic device 100, when the inflatable member 170 inflates, the inflatable member 170 inflates while compressing the auxiliary member 180 against the main body 120, and thus the communication holes 172 and 182 widen in a direction intersecting the longitudinal direction of the auxiliary member 180. In this way, both end portions of the auxiliary member 180 in the longitudinal direction inflate so as to push both end sides of the distal portion 174a of the inflatable member 170, and it is possible to ensure a large area in which the distal side of the inflatable member 170 compresses the skin of the hand H of the patient. For this reason, the hemostatic device 100 can reliably prevent a compression position of the inflatable member 170 against the skin of the hand H from shifting from the puncture site t even in a state where the hemostatic device 100 moves to the wrist side due to movement of the finger of the patient.

The lumen 171 of the inflatable member 170 communicates with a lumen of a tube 193 for supplying a fluid such as air to the inflatable member 170. As illustrated in FIGS. 1 and 3, the tube 193 is connected to the inflatable member 170 on the distal side of the inflatable member 170. The tube 193 is pulled out from the covering member 110 through the inner surface side of the main body 120 and the inner surface side of the first arm portion 130. A position where the tube 193 is pulled out from the inflatable member 170 is not particularly limited. However, as illustrated in FIGS. 1 and 3, when the tube 193 is pulled out from the first end portion 121 side of the main body 120 to the first arm portion 130 side, so that the hemostatic device 100 is attached to the patient, the tube 193 is disposed laterally to the hand H (i.e., in a direction intersecting a direction in which the finger of the hand H extends) (see FIG. 9). For this reason, when the hemostatic device 100 is attached to the patient, the tube 193 can be prevented from interfering with the introducer 200.

The tube 193 may be connected to the auxiliary member 180. Further, a position where the tube 193 is pulled out from the main body 120 can be appropriately changed.

As illustrated in FIGS. 3 and 5, the hemostatic device 100 has the marker portion 105 for aligning the inflatable member 170 with respect to the puncture site t.

The marker portion 105 is disposed at a position corresponding to a substantially center position of the inflatable member 170 (i.e., a center position on the plan view illustrated in FIG. 3, near the proximal portion 184b of the auxiliary member 180).

When the marker portion 105 is disposed so that the center position of the inflatable member 170 and the proximal portion 184b of the auxiliary member 180 are superposed on one another on the cross-sectional view illustrated in FIG. 5, the marker portion 105 can be disposed on the outer surface of the proximal portion 184b of the auxiliary member 180. The marker portion 105 can be disposed on an inner surface of the inflatable member 170 on a side facing the body surface, an inner surface or an outer surface of the inflatable member 170 on the side not facing the body surface, and an internal surface or an external surface of the main body 120 of the covering member 110.

In the marker portion 105, for example, the entire marker portion 105 can be formed of a colored rectangular marker. However, for example, the marker portion 105 may include a transparent central portion and a colored linear frame portion surrounding the central portion. By forming the marker portion 105 in this way, the operator can dispose the marker portion 105 at the puncture site t while checking the puncture site t through the transparent central portion of the marker portion 105. For this reason, the operator can easily dispose the center position of the inflatable member 170 at the puncture site t using the marker portion 105. The specific shape and color of the marker portion 105, a method of forming the hemostatic device 100 on each portion, etc. are not particularly limited.

In an embodiment, the inflatable member 170 is formed of two sheet-shaped members. For example, the inflatable member 170 can be formed by bonding outer peripheral edges of the two sheet-shaped members in a state where the lumen 171 is formed between the two sheet-shaped members formed in a substantially rectangular shape. Similarly to the inflatable member 170, the auxiliary member 180 can be formed of two substantially rectangular sheet-shaped members bonded together.

A method of bonding the sheet-shaped members forming the inflatable member 170 and a method of bonding the sheet-shaped members forming the auxiliary member 180 are not particularly limited. For example, it is possible to adopt adhesion or welding. In addition, a method of securing the inflatable member 170 and the auxiliary member 180, and a method of connecting the inflatable member 170 and the auxiliary member 180 to the main body 120 of the covering member 110 are not particularly limited. For example, it is possible to adopt adhesion or welding.

The inflatable member 170 and the auxiliary member 180 are not limited to a structure in which a plurality of sheet-shaped members is bonded. For example, the inflatable member 170 and the auxiliary member 180 may be formed of a single bag-shaped member having a space, through which a fluid can flow, formed therein.

A material used for the inflatable member 170 and the auxiliary member 180 is not particularly limited, and examples thereof may include similar materials to those exemplified as the material of the covering member 110.

<Injection Portion>

As illustrated in FIGS. 1 and 2, the hemostatic device 100 has an injection portion 191 for injecting a fluid into the inflatable member 170.

The injection portion 191 includes a connector having an incorporated check valve (not illustrated). A syringe (not illustrated) can be connected to the injection portion 191.

A cushioning member 192 having an inflatable space is disposed between the injection portion 191 and the inflatable member 170. The cushioning member 192 includes a flexible bag-shaped member having a space formed inside. The cushioning member 192 may be provided with an arrow-shaped marker indicating a direction in which the syringe is inserted into the injection portion 191.

The injection portion 191 is connected to one end side of the cushioning member 192. A lumen of the injection portion 191 communicates with the space in the cushioning member 192. However, while the check valve incorporated in the injection portion 191 is closed, communication between the lumen of the injection portion 191 and the space in the cushioning member 192 is cut off.

A flexible tube 193 is connected to the other end side of the cushioning member 192. A lumen of the tube 193 communicates with the space in the cushioning member 192. Further, in the tube 193, the other end portion opposite to one end portion connected to the cushioning member 192 is connected to the inflatable member 170. The lumen of the tube 193 communicates with the lumen 171 of the inflatable member 170.

For example, the other end portion of the tube 193 can be connected to the inflatable member 170 using an adhesive, etc. while being interposed between the two sheet-shaped members forming the inflatable member 170. In the sheet-shaped members forming the inflatable member 170, for example, convex portions partially protruding outward from the sheet-shaped members may be formed at parts interposing the tube 193 therebetween.

To inflate the inflatable member 170 and the auxiliary member 180, the operator inserts a distal tubular portion of a syringe (not illustrated) into the injection portion 191 to open the check valve. For example, the operator injects air in the syringe into the lumen 171 of the inflatable member 170 by pushing a plunger of the syringe in a state where the check valve of the injection portion 191 is open.

When air is injected into the lumen 171 of the inflatable member 170, the inflatable member 170 inflates. Further, the air injected into the lumen 171 of the inflatable member 170 flows into the lumen 181 of the auxiliary member 180 via the communication hole 172 of the inflatable member 170 and the communication hole 182 of the auxiliary member 180. When air flows into the lumen 181 of the auxiliary member 180, the auxiliary member 180 inflates. When the inflatable member 170 and the auxiliary member 180 inflate, the cushioning member 192 communicating with the lumen 171 of the inflatable member 170 via the tube 193 expands.

The space in cushioning member 192 and the lumen 171 of the inflatable member 170 are in communication with each other via the tube 193 at all times. The injection portion 191 maintains the check valve incorporated in the injection portion 191 in a closed state when the syringe is not inserted into the injection portion 191 to prevent air from leaking from the injection portion 191. For this reason, in the hemostatic device 100, when the patient moves the hand H in a state where the hemostatic device 100 is worn on the patient, the inflatable member 170 and the auxiliary member 180 compressing the puncture site t on the hand H are deformed. When there is no escape place for air in the lumen 171 of the inflatable member 170 and the lumen 181 of the auxiliary member 180 during deformation of the inflatable member 170 and the auxiliary member 180, deformation of the inflatable member 170 and the auxiliary member 180 is hindered. For this reason, the patient's movement of the hand H is restricted. The cushioning member 192 included in the hemostatic device 100 allows air to move from the lumen 171 of the inflatable member 170 and the lumen 181 of the auxiliary member 180 to the cushioning member 192 when the patient moves the hand H. For this reason, it is possible to restrict the movable range of the patient's hand H by the inflatable member 170 and the auxiliary member 180. When the patient returns the hand H from the deformed state to the original state, air moves from the cushioning member 192 to the inflatable member 170. Therefore, the compressive force can be effectively applied to the puncture site t from the inflatable member 170.

When the operator contracts the inflatable member 170 and the auxiliary member 180, the operator inserts the distal tubular portion of the syringe into the injection portion 191 and pulls the plunger of the syringe. By performing the above operation, the operator can discharge the air in the inflatable member 170 and the air in the auxiliary member 180 to the syringe.

When the operator inflates the inflatable member 170, the operator can visually confirm that the inflatable member 170 and the auxiliary member 180 can be pressurized without leakage of air by confirming expansion of the cushioning member 192.

Next, usage examples of the hemostatic device 100 will be described with reference to FIGS. 8 to 11. In the following, a description will be given of an example of a procedure for attaching the hemostatic device 100 to the left hand H of the patient on which the puncture site t is formed.

Figure 8:
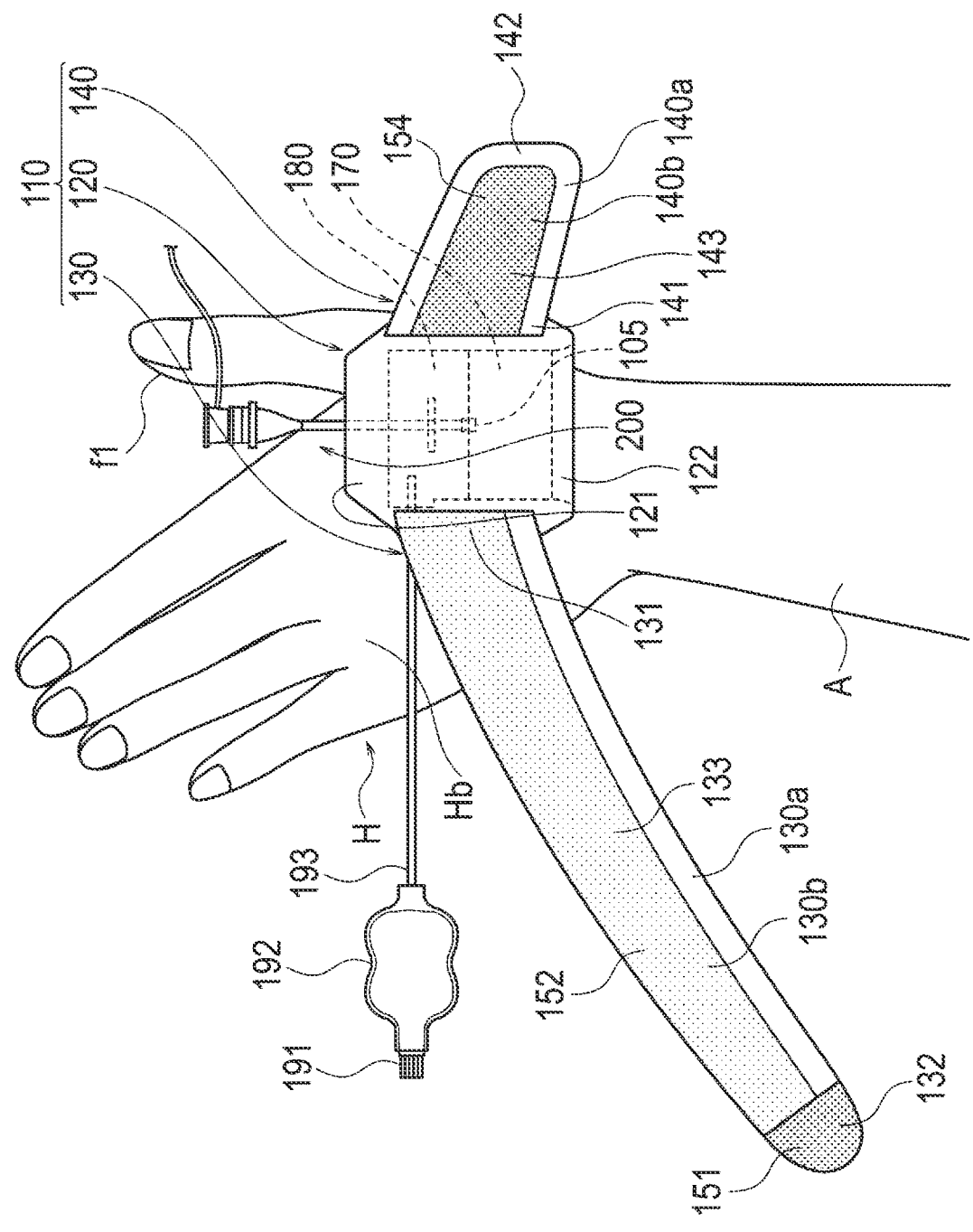
FIG. 8 is a diagram schematically illustrating a usage example of the hemostatic device.

FIG. 8 illustrates a state after performing various procedures by inserting the sheath tube of the introducer 200 into the distal radial artery side of the palmar artery B via the puncture site t (see FIG. 11) formed on the dorsal side Hb of the hand H of the patient. In addition, FIG. 8 illustrates a state in which a part of the sheath tube of the introducer 200 is pulled out from the puncture site t after completing the above procedures.

At the start of hemostasis, as illustrated in FIG. 8, the operator disposes the main body 120 of the covering member 110 so as to overlap the side of the dorsal side Hb of the hand H of the patient. In this instance, the marker portion 105 formed at a substantially center position of the inflatable member 170 is disposed at the puncture site t.

Subsequently, as illustrated in FIG. 9, the operator wraps the main body region 133 of the first arm portion 130 along an outer circumference of the hand H of the patient. The operator brings the third securing member 153 disposed on the inner surface of the first arm portion 130 into contact with the fourth securing member 154 disposed on the outer surface of the second arm portion 140 while wrapping the main body region 133 of the first arm portion 130 along the outer circumference of the hand H of the patient, thereby securing the first arm portion 130 and the second arm portion 140 via the respective securing members 153 and 154.

Subsequently, as illustrated in FIG. 10, the operator folds a part of the first arm portion 130 not fixed to the second arm portion 140 back to the palm side of the hand H of the patient. In this instance, the operator can bring the first securing member 151 disposed on the outer surface of the first arm portion 130 into contact with the second securing member 152 disposed on the outer surface of the first arm portion 130, so that a surplus part of the first arm portion 130 not wrapped around the hand H is secured via the respective securing members 151 and 152 in a folded state illustrated in FIG. 10.

Through the above procedure, as illustrated in FIG. 10, the operator can secure the hemostatic device 100 to the hand H of the patient. FIG. 10 illustrates a state in which the introducer 200 is completely removed from the puncture site t.

Subsequently, the operator inflates the inflatable member 170 and the auxiliary member 180 by connecting a syringe to the injection portion 191 and injecting air into the inflatable member 170. In the hemostatic device 100, when the inflatable member 170 and the auxiliary member 180 are inflated, the inflatable member 170 applies a compressive force to the puncture site t. After inflating the inflatable member 170 and the auxiliary member 180, the operator removes the sheath tube of the introducer 200 from the puncture site t as illustrated in FIG. 10. In this instance, since the first arm portion 130 and the second arm portion 140 are disposed along an outer peripheral direction of the hand H of the patient, the arm portions 130 and 140 do not overlap with the sheath tube of the introducer 200. For this reason, after inflating the inflatable member 170 and the auxiliary member 180, the operator can easily remove the sheath tube of the introducer 200 from the puncture site t.

The operator confirms that there is no bleeding from the puncture site t while hemostasis is performed using the hemostatic device 100. When there is bleeding from the puncture site t, the operator adjusts the amount of air injected into the inflatable member 170 and the auxiliary member 180.

As illustrated in FIG. 11, in a state where the hemostatic device 100 is worn on the hand H of the patient, a distal side part of the inflatable member 170 and the auxiliary member 180 are disposed on the fingertip side of the hand H. In addition, a proximal side part of the inflatable member 170 is disposed on the wrist side of the hand H. Since the proximal portion 174b of the inflatable member 170 is connected to the second end portion 122 of the main body 120 of the covering member 110, an edge portion that may bite into the surface of the hand H of the patient is not formed in the proximal portion 174b of the inflatable member 170. For this reason, it is possible to prevent the proximal portion 174b of the inflatable member 170 from coming into contact with the skin of the hand H of the patient.

Figure 12:
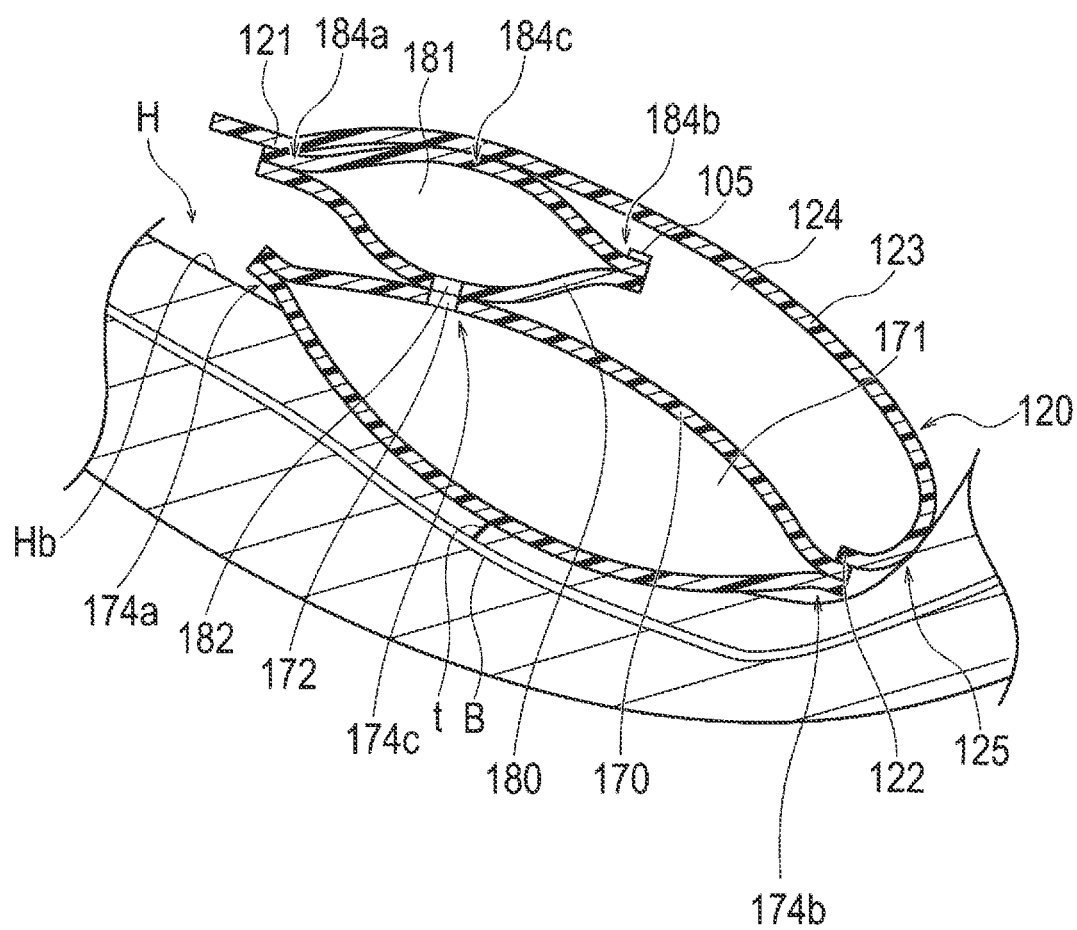
FIG. 12 is a cross-sectional view schematically illustrating the hemostatic device worn on a hand of a patient in a state where the patient bends the hand.

Here, FIG. 12 illustrates a state in which the hand H of the patient is bent toward the side of the dorsal side Hb of the hand H (i.e., the upper side in FIG. 12) while the hemostatic device 100 is worn on the hand H of the patient. In the main body 120, when the hand H of the patient is bent and the shape of the hand H is deformed during inflation of the inflatable member 170 while the hemostatic device 100 is worn on the hand H of the patient, the curved region 125 is deformed to be folded following a change in the shape of the hand H. When the curved region 125 is deformed to be folded, a part of the curved region 125 is disposed on the proximal side (i.e., the wrist side) of the proximal portion 174b of the inflatable member 170. For this reason, when the patient wearing the hemostatic device 100 moves the hand H, it is possible to prevent the curved region 125 of the main body 120 from coming into contact with the surface of the hand H, and the proximal portion 174b of the inflatable member 170 from being strongly pressed against the surface of the hand H of the patient.

When the inflatable member 170 and the auxiliary member 180 are inflated, the auxiliary member 180 applies an oblique force toward the puncture site t side so as to compress the distal portion 174a side of the inflatable member 170. For this reason, the hemostatic device 100 can effectively increase the compressive force applied to the puncture site t by the inflatable member 170.

After a certain period of time passes after start of hemostasis, the operator gradually depressurizes the inflatable member 170 and the auxiliary member 180 to confirm that hemostasis at the puncture site t is properly performed. After the hemostasis at the puncture site t is completed, the operator sufficiently depressurizes the inflatable member 170 and the auxiliary member 180. Then, the operator releases securing of the hemostatic device 100 by the first arm portion 130 and the second arm portion 140, and removes the hemostatic device 100 from the hand H of the patient.

In the hemostatic device 100, as illustrated in FIG. 10, during hemostasis, while the arm portions 130 and 140 are secured in a wrapped state along the outer circumference of the hand H of the patient, fingers of the patient can be allowed to project toward the distal side of the main body 120 of the covering member 110. For this reason, since each finger is not covered by the covering member 110 in the state where the hemostatic device 100 is worn on the hand H, the patient can freely move the fingers while hemostasis is performed.

The operator can easily attach the hemostatic device 100 to the patient within a short time using the first arm portion 130 and the second arm portion 140 by proceeding with an attachment operation according to the procedure illustrated in FIGS. 8 to 10. Further, in the hemostatic device 100, the covering member 110 can be secured to the hand H of the patient using the securing members 151, 152, 153, 154, and 155 disposed on the respective arm portions 130 and 140. For this reason, the hemostatic device 100 can reduce a burden on the skin of the patient during wearing when compared to a hemostatic device secured to the hand H or the forearm A of the patient using a seal member provided with an adhesive material, etc.

Further, since the hemostatic device 100 includes the inflatable member 170 that applies a compressive force to the puncture site t, the compressive force can be easily adjusted by adjusting the internal pressure of the inflatable member 170. Further, in the hemostatic device 100, even when the inflatable member 170 is deformed so as to change the internal pressure following movement of the hand H when the patient moves the hand H, the deformable auxiliary member 180 mitigates the change in the internal pressure of the inflatable member 170. For this reason, the inflatable member 170 has a high following property to movement of the hand H of the patient, and compression on the puncture site t by the inflatable member 170 can be appropriately maintained.

Further, the hemostatic device 100 covers only a part of the hand H of the patient by the covering member 110, and does not cover the entire hand H. For this reason, when the patient moves the hand H in the state where the hemostatic device 100 is worn on the hand H of the patient, it is possible to prevent movement of the hand H of the patient from being transmitted to the entire hemostatic device 100. Therefore, the hemostatic device 100 can suppress misalignment from the hand H of the patient when the patient moves the hand H in the state where the hemostatic device 100 is worn on the hand H of the patient.

Hereinafter, effects of the above-described embodiments will be described.

The hemostatic device 100 includes the covering member 110 disposed to cover the puncture site t on the hand H of the patient, the plurality of securing members 151, 152, 153, 154, and 155 for securing the covering member 110 in a state where the covering member 110 covers the puncture site t, the inflatable member 170 connected to the covering member 110 and inflated by injection of a fluid, and the auxiliary member 180 which has a smaller outer shape than that of the inflatable member 170 and is deformable. The covering member 110 includes the main body 120 to which the inflatable member 170 is connected, the first arm portion 130 protruding from the main body 120, and the second arm portion 140 protruding from a position facing the first arm portion 130 with the main body 120 interposed therebetween. The main body 120 includes the first end portion 121 located on the distal side of the main body 120 between the first arm portion 130 and the second arm portion 140, and the second end portion 122 located on the proximal side of the main body 120. The inflatable member 170 is connected to the second end portion 122, and the auxiliary member 180 is connected to the first end portion 121 in a state of being interposed between the main body 120 and the inflatable member 170.

In the hemostatic device 100 configured as described above, since the auxiliary member 180 is connected to the first end portion 121 of the main body 120 located on the distal side of the inflatable member 170, when the patient moves the hand H in the state where the inflatable member 170 is inflated, the proximal portion 174b of the inflatable member 170 located on the proximal side of the proximal portion 184b of the auxiliary member 180 easily comes into contact with the surface of the hand. However, in the hemostatic device 100, since the inflatable member 170 is connected to the second end portion 122 of the main body 120 located on the proximal side of the inflatable member 170, an edge portion that may bite into the surface of the hand H of the patient is not formed at the proximal portion 174b (i.e., the outer peripheral edge) of the inflatable member 170. In this way, even when the patient moves the hand in the state where the inflatable member 170 is inflated, the hemostatic device 100 can prevent the proximal portion 174b (i.e., the outer peripheral edge) of the inflatable member 10 from biting into the hand, and thus it is possible to reduce the pain of the patient during hemostasis.

In addition, since the hemostatic device 100 includes the auxiliary member 180 that compresses the inflatable member 170 on the distal side of the inflatable member 170, it is possible to ensure a large area in which the inflatable member 170 compresses the hand H of the patient on the distal side of the inflatable member 170. For this reason, in the inflatable member 170, even when the hemostatic device 100 moves to the wrist side due to movement of the finger of the patient, etc., it is possible to prevent the puncture site t from shifting from a range in which the inflatable member 170 applies the compressive force to the hand.

In addition, since the auxiliary member 180 compresses the inflatable member 170 on the distal portion 174a side of the inflatable member 170, the hemostatic device 100 performs compression so that rising of the distal portion 174a of the inflatable member 170 is prevented and the distal portion 174a side of the inflatable member 170 comes into contact with the surface of the hand H in a large area. For this reason, when the auxiliary member 180 presses the inflatable member 170, the hemostatic device 100 can ensure a large area in which the distal portion 174*a* side of the inflatable member 170 compresses the surface of the hand H while preventing rising of the inflatable member 170 and prevent the inflatable member 170 from shifting from the puncture site t. In addition, the auxiliary member 180 prevents misalignment of the inflatable member 170 with respect to the hand H by pressing a part of the inflatable member 170 against the hand H.

When hemostasis is performed at the puncture site t on the hand H, the hemostatic device 100 worn on the hand H does not shift to the distal side of the hand H due to the shape of the hand H since when the hand H is expanded, the shape of the hand H becomes wider toward the fingertip side. However, the hemostatic device 100 may shift to the proximal side of the hand H. In the hemostatic device 100, the inflatable member 170 compresses a large area of the hand H located on the fingertip side of the puncture site t. For this reason, even when the hemostatic device 100 is shifted to the wrist side, the hemostatic device 100 can prevent the puncture site t from shifting from the range in which the inflatable member 170 applies a compressive force to the hand H.

In addition, in the hemostatic device 100, the inflatable member 170 is connected to the main body 120 at a different position from that of the first arm portion 130 and the second arm portion 140 wrapped along the outer circumference of the hand H of the patient, and the first arm portion 130 and the second arm portion 140 are connected to positions facing each other with the main body 120 interposed therebetween. For this reason, in the hemostatic device 100, when the hand H is moved while the hemostatic device 100 is worn on the hand H of the patient, the fluid located inside the inflatable member 170 easily moves along a longitudinal direction of the first arm portion 130 and the second arm portion 140 (i.e., the right-left direction of FIG. 3). In this way, in the inflatable member 170, since the end portion of the inflatable member 170 on the first arm portion 130 side and the end portion of the inflatable member 170 on the second arm portion 140 side are pressed against the surface of the hand of the patient by the main body 120 of the covering member 110, it is possible to increase the compression area of the inflatable member 170 with respect to the puncture site t.

Further, in the hemostatic device 100, the inflatable member 170 is connected to the first end portion 121 of the main body 120, and the auxiliary member 180 is connected to the second end portion 122 of the main body 120 so as to face the inflatable member 170 with the main body 120 interposed therebetween. For this reason, the inflatable member 170 and the auxiliary member 180 have different connection positions with respect to the main body 120, and thus easily follow movement of the hand H, etc. In addition, the inflatable member 170 is deformed with respect to a contact position between the inflatable member 170 and the auxiliary member 180 in a state where the hemostatic device 100 is worn and the inflatable member 170 is inflated, and thus is easily deformed following movement of the hand H.

Further, in the hemostatic device 100, since the auxiliary member 180 having a smaller outer shape than that of the inflatable member 170 is disposed between the main body 120 and the inflatable member 170, the auxiliary member 180 can adjust a compressive force applied to the hand H by a predetermined position of the inflatable member 170. For this reason, the hemostatic device 100 can suitably apply the compressive force to the hand H by the predetermined position of the inflatable member 170.

Further, the auxiliary member 180 is connected to the inflatable member 170 at a position biased toward one end side (i.e., the distal portion 174*a* side) of the inflatable member 170. For this reason, the hemostatic device 100 can reliably prevent rising of the distal portion 174*a* side of the inflatable member 170 when the inflatable member 170 is inflated, and prevent misalignment between the inflatable member 170 and the auxiliary member 180 during inflation of the inflatable member 170.

In addition, to apply an oblique force to compress the distal portion 174*a* side of the inflatable member 170, the auxiliary member 180 covers the distal portion 174*a* side of the inflatable member 170, and inhibits an inflation force of the inflatable member 170 from escaping to the outside of the main body 120.

Furthermore, since the auxiliary member 180 for compressing the inflatable member 170 is provided on the distal portion 174*a* side of the inflatable member 170, it is possible to ensure a large area in which the distal portion 174*a* side of the inflatable member 170 compresses the skin of the hand H of the patient. In this way, even in a state where the hemostatic device 100 is moved to the wrist side due to movement of the finger of the patient, it is possible to prevent the compression position of the inflatable member 170 with respect to the skin of the hand H from shifting from the puncture site t.

In addition, the auxiliary member 180 is an auxiliary inflatable portion inflatable by injection of a fluid, and the auxiliary inflatable portion is connected to the inflatable member 170 in a state of communicating with the inflatable member 170. For this reason, when the hemostatic device 100 is worn, the auxiliary member 180 can be contracted, and thus it is possible to easily align the hemostatic device 100 with respect to the puncture site t. In addition, since the inflatable member 170 and the auxiliary member 180 communicate with each other, the inflatable member 170 and the auxiliary member 180 can be inflated at the same time by injecting a fluid into the inflatable member 170, which can reduce the labor of the operator.

Further, the inflatable member 170 is connected to the center portion 184*c* of the auxiliary member 180. For this reason, in the hemostatic device 100, even in the state where the inflatable member 170 is inflated, the inflatable member 170 can be flexibly deformed along a connection portion with the auxiliary member 180. In this way, when the hand H of patient moves, the inflatable member 170 can follow the change in the shape of the hand H, and appropriately maintain the compressive force on the puncture site t on the hand H of the patient.

In addition, the main body 120 is connected to the proximal portion 174*b* of the inflatable member 170 (i.e., the peripheral edge located at the end portion of the inflatable member 170 on the proximal side) and the distal portion 184*a* of the auxiliary member 180 (i.e., the peripheral edge located at the end portion of the auxiliary member 180 on the distal side). For this reason, in the hemostatic device 100, steps are formed at a connection position between the main body 120 and the proximal portion 174*b* of the inflatable member 170 and a connection position between the main body 120 and the distal portion 184*a* of the auxiliary member 180. However, an edge portion that may bite into the surface of the hand H of the patient is not formed at the proximal portion 174*b* (i.e., the outer peripheral edge) of the inflatable member 170 and the distal portion 184*a* (i.e., the outer peripheral edge) of the auxiliary member 180. In this way, when the patient moves the hand H, in the state where the inflatable member 170 is inflated, the hemostatic device 100 can prevent an edge of the peripheral edge of the inflatable member 170 and an edge of the peripheral edge of the auxiliary member 180 from coming into contact with the skin of the hand H of the patient and causing pain due to biting, etc. In addition, in the hemostatic device 100, since the main body 120 is connected to the proximal portion 174b of the inflatable member 170 and the distal portion 184a of the auxiliary member 180, the inflatable member 170 and the auxiliary member 180 are located on the internal surface side of the main body 120 in the state where the inflatable member 170 is inflated. For this reason, the hemostatic device 100 can suitably transmit the compressive force of the inflatable member 170 to the puncture site t.

Further, the main body 120 has the curved region 125 on the second end portion 122 side, and the inflatable member 170 is connected to the curved region 125. Since the curved region 125 is formed in the main body 120, the space 124 can be formed between the main body 120 and the inflatable member 170. By having the space 124, the main body 120 is deformed so that the curved region 125 is folded when the inflatable member 170 is inflated, and the second end portion 122 of the main body 120 is curved toward the first end portion 121 side of the main body 120. For this reason, when the inflatable member 170 is inflated, it is possible to more reliably prevent the second end portion 122 of the main body 120 from biting into the skin of the hand H of the patient.

Further, in the first arm portion 130, the wall thickness of the peripheral edge 130a of the first arm portion 130 on the proximal side is smaller than the wall thickness of the center portion 130b of the first arm portion 130. In the second arm portion 140, the wall thickness of the peripheral edge 140a of the second arm portion 140 on the proximal side is smaller than that of the center portion 140b of the second arm portion 140. For this reason, in the hemostatic device 100, the wall thicknesses of the peripheral edges 130a and 140a located on the wrist side of the respective arm portions 130 and 140, which serve as start points of movement of the finger when the patient moves the finger in the state where the hemostatic device 100 is worn on the hand H of the patient, are small. In this way, the hemostatic device 100 can prevent the peripheral edges 130a and 140a of the respective arm portions 130 and 140 from biting into the skin of the hand H when the patient moves the hand H.

Further, the first arm portion 130 is longer than the second arm portion 140. For this reason, in the hemostatic device 100, when the hemostatic device 100 is worn on the hand H of the patient, securing positions of the first arm portion 130 and the second arm portion 140 are located on the palm side of the hand H or the side of the dorsal side Hb of the hand H, and thus the inflatable member 170 can be more reliably secured to the hand H of the patient by the first arm portion 130 and the second arm portion 140.

Next, a description will be given of Modification Example 1 and Modification Example 2 of the hemostatic device according to the above-described embodiments. In the description of each of the modification examples, detailed description of a configuration, etc. previously described in the embodiments will be omitted. Further, content not particularly described in the description of the modification examples can be regarded as similar content to that of the embodiments.

Figure 14:
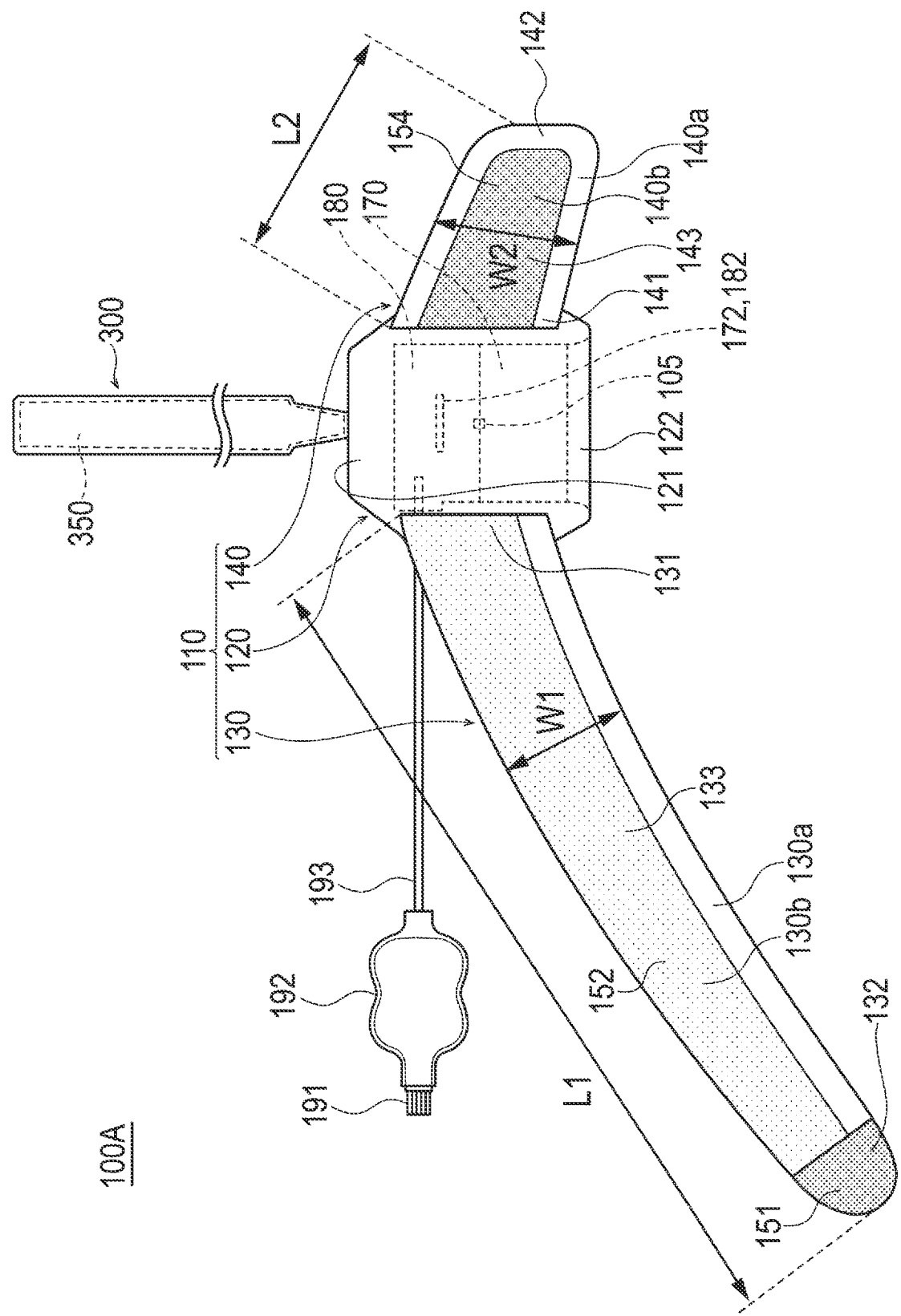
FIG. 14 is a plan view of a hemostatic device according to Modification Example 1, seen from an outer surface side of a main body of a covering member.

FIG. 14 illustrates a hemostatic device 100A according to Modification Example 1. The hemostatic device 100A according to Modification Example 1 includes a third arm portion 300 protruding from the main body 120 of the covering member 110 at a different position from that of the first arm portion 130 and the second arm portion 140. Specifically, the third arm portion 300 protrudes from the first end portion 121 side of the main body 120 of the covering member 110.

Figure 15:
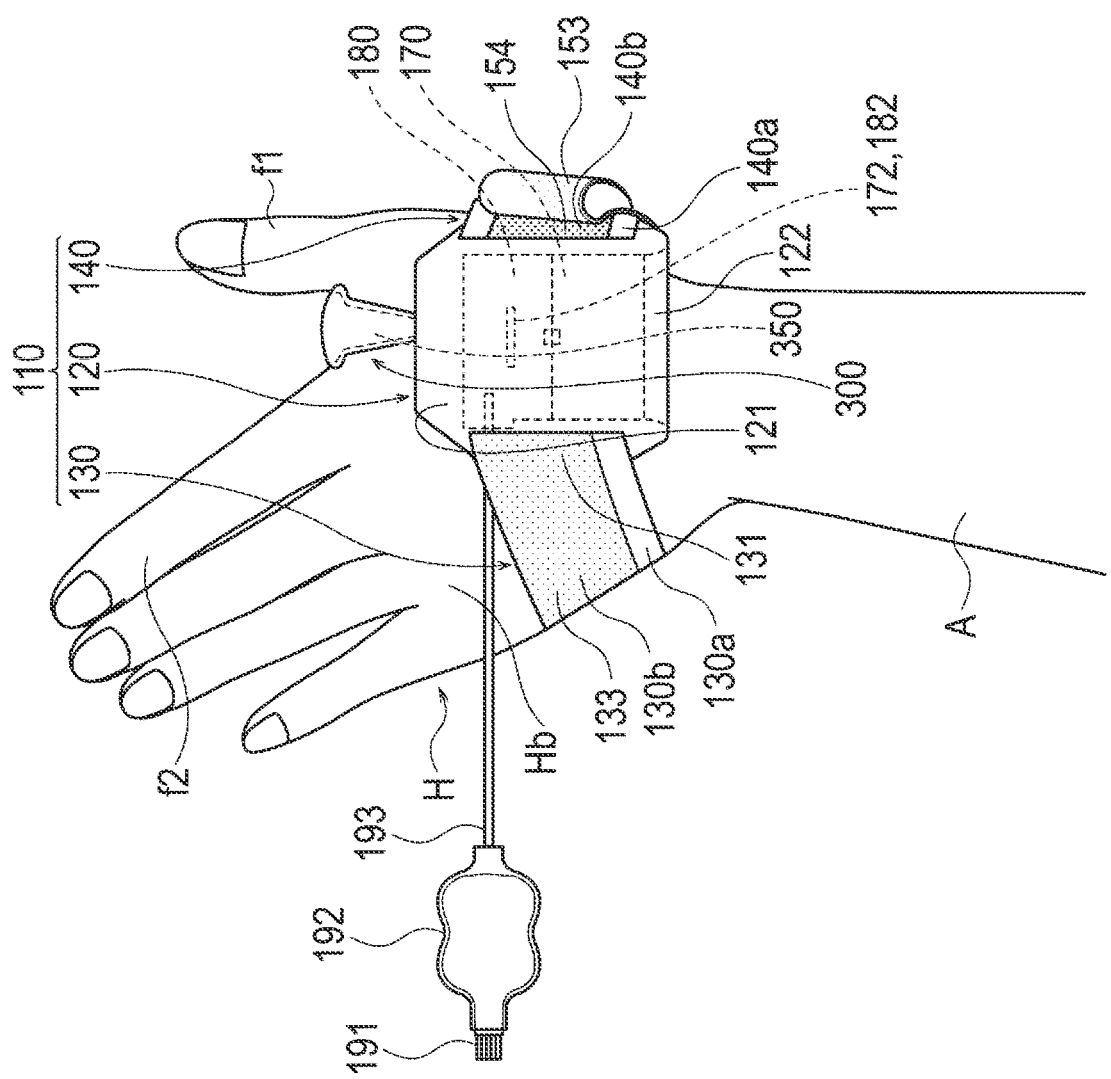
FIG. 15 is a diagram schematically illustrating the hemostatic device according to Modification Example 1 that is worn on the hand of the patient.

As illustrated in FIG. 15, the third arm portion 300 can be disposed between or at an inter-finger portion of adjacent fingers f1 and f2 of the hand H of the patient in a state where the hemostatic device 100A is worn on the hand H of the patient. The third arm portion 300 is formed of a flexible member that can be deformed along the shape of the outer surface of the hand H of the patient. Even though the third arm portion 300 can be disposed in an inter-finger portion between the thumb f1 and the index finger f2 in the hemostatic device 100A, the third arm portion 300 may be disposed in an inter-finger portion located between other fingers.

The third arm portion 300 includes a securing member 350 that can be connected to the first arm portion 130 on the inner surface side of the third arm portion 300. The securing member 350 of the third arm portion 300 can be connected to the second securing member 152 of the first arm portion 130. For this reason, the third arm portion 300 can be secured to the first arm portion 130 by bringing the securing member 350 disposed on the inner surface side of the third arm portion 300 into contact with the second securing member 152 of the first arm portion 130. Therefore, as illustrated in FIG. 15, after securing the first arm portion 130 and the second arm portion 140 via the respective securing members 152 and 154 while wrapping the first arm portion 130 along the outer circumference of the hand H of the patient, the operator passes the third arm portion 300 between the thumb f1 and the index finger f2 of the hand H of the patient, and superimposes a part of the third arm portion 300 on the palm side of the hand H of the patient on the first arm portion 130 wrapped along the outer circumference of the hand H of the patient. In this way, by bringing the securing member 350 disposed on the inner surface side of the third arm portion 300 into contact with the second securing member 152 of the first arm portion 130, the operator can secure the first arm portion 130 and the third arm portion 300 via the securing member 152 and the securing member 350 of the third arm portion 300. According to such a configuration, by securing the third arm portion 300 to the first arm portion 130 through between the fingers f1 and f2 of the patient, the hemostatic device 100A can effectively prevent the inflatable member 170 from rising on the distal side of the hand H while effectively preventing misalignment of the inflatable member 170 with respect to the puncture site t. For this reason, even when the hand H is moved in the state where the inflatable member 170 is inflated, by securing the first arm portion 130 and the second arm portion 140 and securing the third arm portion 300 and the first arm portion 130, the hemostatic device 100A can effectively prevent rising of the distal side of the main body 120 to which the inflatable member 170 is connected, and appropriately maintain the compressive force of the inflatable member 170 on the puncture site t of the hand H.

The securing member 350 of the third arm portion 300 is formed of the male side of the surface fastener. The surface fastener is a fastener that is removable in terms of surface, and is, for example, MAGIC TAPE® or VELCRO®.

A configuration of the securing member 350 of the third arm portion 300 is not limited as long as the securing member 350 can be secured to the first arm portion 130 wrapped around the limb of the patient. For example, a position where the securing member 350 is disposed on the third arm portion 300 can be changed as appropriate. Further, when the securing members 151, 152, 153, 154, and 155 and the securing member 350 of the third arm portion 300 include surface fasteners, the male side and the female side of the surface fasteners may be interchanged. Further, the securing members 151, 152, 153, 154, and 155 and the securing member of the third arm portion 300 may be snaps, buttons, clips, frame members in which holes are formed, etc.

In the hemostatic device 100A according to Modification Example 1, the covering member 110 is formed by the main body 120 and the arm portions 130, 140, and 300 as separate members. The main body 120 and the third arm portion 300 can be connected by, for example, adhesion, welding, etc. However, in the hemostatic device 100A, any part of the main body 120, the first arm portion 130, the second arm portion 140, and the third arm portion 300 of the covering member 110 may be integrally formed of one member.

Figure 16:
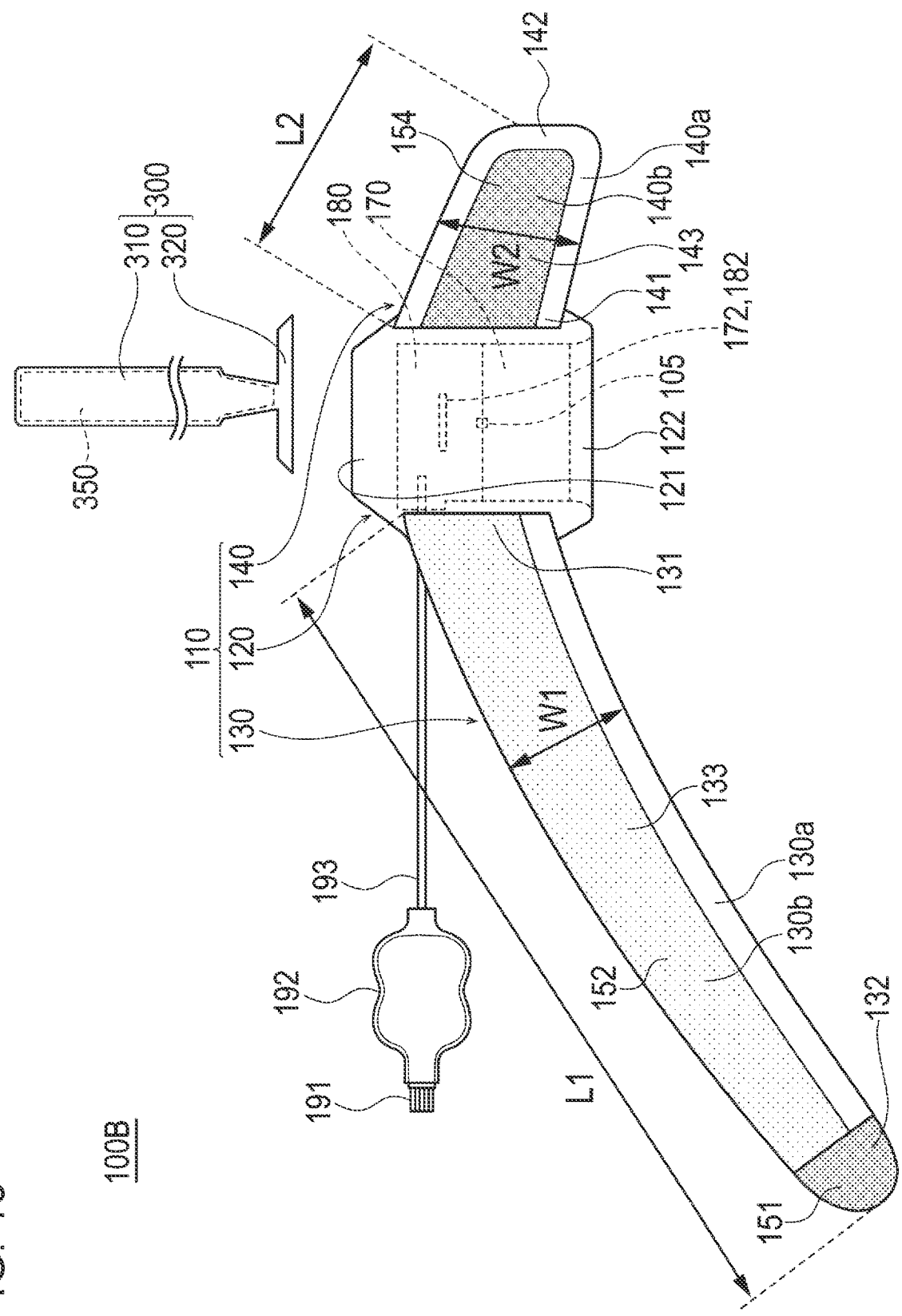
FIG. 16 is a plan view of a hemostatic device according to Modification Example 2 in a state before a third arm portion is connected to a main body of a covering member.
Figure 17:
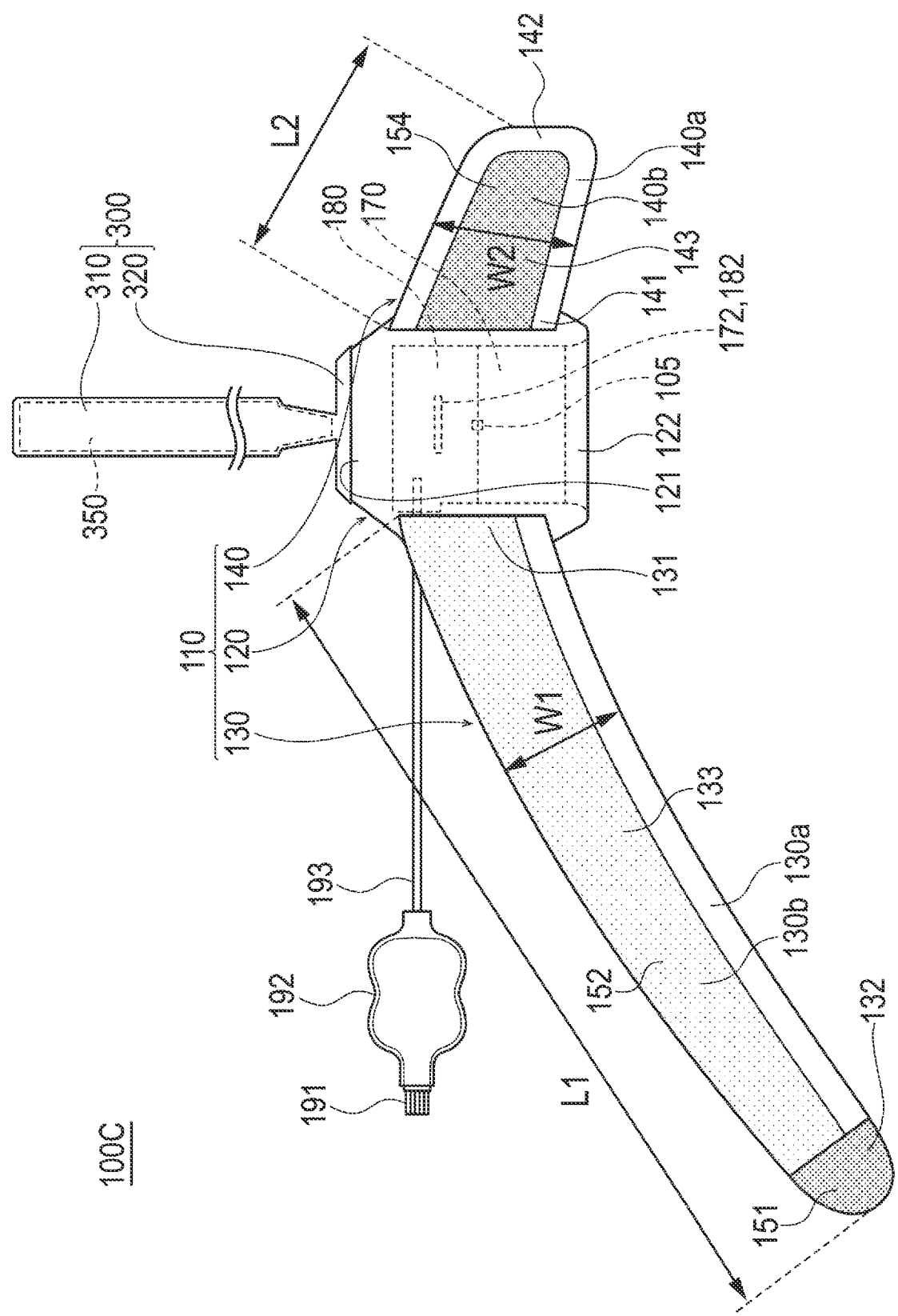
FIG. 17 is a plan view of the hemostatic device according to Modification Example 2 in a state where the third arm portion is connected to the main body of the covering member.

FIGS. 16 and 17 illustrate a hemostatic device 100B according to Modification Example 2. In the hemostatic device 100B according to Modification Example 2, the third arm portion 300 is detachable from and connectable to the main body 120 of the covering member 110. FIG. 16 illustrates a state before the third arm portion 300 is connected to the main body 120 of the covering member 110, and FIG. 17 illustrates a state in which the third arm portion 300 is connected to the main body 120 of the covering member 110.

The third arm portion 300 includes a main body 310 and a connection portion 320 disposed on one end side of the main body 310. The main body 310 of the third arm portion 300 includes a securing member 350 connectable to the first arm portion 130 on the inner surface side of the third arm portion 300. For this reason, the securing member 350 of the main body 310 can be connected to the second securing member 152 of the first arm portion 130. Further, the connection portion 320 of the third arm portion 300 can be connected to the first end portion 121 side of the main body 120 of the covering member 110. For example, the connection portion 320 of the third arm portion 300 is attachable to the main body 120 of the covering member 110 by an adhesive material, a bonding material, etc. on the inner surface side or the outer surface side of the connection portion 320.

In addition, the connection portion 320 of the third arm portion 300 may be attachable to the main body 120 of the covering member 110 by the male side of the surface fastener disposed on the inner surface side of the connection portion 320 and the female side of the surface fastener disposed on the outer surface side of the first end portion 121 side of the main body 120 of the covering member 110 so that the inner surface side of the connection portion 320 is connected to the outer surface side of the main body 120. In this way, in the hemostatic device 100B, since the third arm portion 300 can be attached to the main body 120 of the covering member 110 at the discretion of the operator, the operator can provide the third arm portion 300 on the hemostatic device 100B according to the condition of the hand H of the patient (for example, the hand H is easily sweated).

A material used for the third arm portion 300 of the covering member 110 of each of the hemostatic device 100A and the hemostatic device 100B is not particularly limited. For example, the same material as that exemplified as the first arm portion 130 and the second arm portion 140 of the covering member 110 can be mentioned.

Even though the hemostatic devices 100, 100A, 100B, and 100C have been described, the invention is not limited to the embodiments described in this specification, and can be appropriately modified based on description of the scope of claims.

In the description of the embodiments, the hemostatic device for performing hemostasis at the puncture site formed on the dorsal side of the left hand has been exemplified. However, the hemostatic device can be used to perform hemostasis on a puncture site formed on a dorsal side of a right hand, a puncture site formed on a palm of the right hand, a puncture site formed on a palm of the left hand, etc.

The auxiliary member is not limited to the inflatable member described in each embodiment. For example, the auxiliary member may include a member made of a resin material such as plastic, gel, etc., a member containing gel whose moisture content decreases over time to gradually reduce a compressive force, an elastic material such as a sponge-like substance, an aggregate of fibers such as cotton, metal, a member having a predetermined three-dimensional shape (sphere, ellipsoid, triangular pyramid, etc.), an appropriate combination thereof, etc.

In addition, the shape, dimensions, etc. of each portion of the hemostatic device are not particularly limited and can be changed as appropriate as long as the inflatable member can be disposed at the site where bleeding is to be stopped while wrapping the first arm portion and the second arm portion around at least a part of the limb including the hand.

What is claimed is:

1. A hemostatic device attachable to a hand of a patient, comprising:
    a covering member configured to cover a site where bleeding is to be stopped on a hand of a patient;
    a securing member configured to secure the covering member to the hand when the covering member covers the site;
    an inflatable member connected to the covering member and inflatable by injection of a fluid; and
    a deformable auxiliary member having a smaller outer shape than an outer shape of the inflatable member, wherein
    the covering member includes a main body, a first arm portion protruding from a first side of the main body, and a second arm portion protruding from a second side of the main body, wherein the first and second sides are opposite sides of the main body,
    the main body includes a first end portion located on a distal side of the main body between the first arm portion and the second arm portion, and a second end portion located on a proximal side of the main body between the first arm portion and the second arm portion,
    the inflatable member is connected to the second end portion of the main body, and
    the auxiliary member is connected to the first end portion of the main body and is interposed between the main body and the inflatable member, the auxiliary member being located closer to a distal end of the main body than a proximal end thereof.

2. The hemostatic device according to claim 1, wherein the auxiliary member is connected to a portion of the inflatable member that is located closer to a distal end of the inflatable member than a proximal end thereof.

3. The hemostatic device according to claim 1, wherein the auxiliary member is inflated when the inflatable member is inflated as a result of being in a state of fluid communication with the inflatable member.

4. The hemostatic device according to claim 3, wherein the inflatable member is connected to a center portion of the auxiliary member.

5. The hemostatic device according to claim 4, wherein the inflatable member and the auxiliary member are connected via a communication hole through which the fluid passes.

6. The hemostatic device according to claim 5, wherein the communication hole extends along a line parallel to the distal end of the main body.

7. The hemostatic device according to claim 1, wherein the main body is connected to a peripheral edge of the inflatable member and a peripheral edge of the auxiliary member.

8. The hemostatic device according to claim 1, wherein the main body has a curved region at the second end portion, and the inflatable member is connected to the curved region.

9. The hemostatic device according to claim 1, wherein
  a wall thickness of a peripheral edge of the first arm portion on a proximal side is smaller than a wall thickness of a center portion of the first arm portion, and
  a wall thickness of a peripheral edge of the second arm portion on a proximal side is smaller than a wall thickness of a center portion of the second arm portion.

10. The hemostatic device according to claim 1, wherein the first arm portion is longer than the second arm portion.

11. A hemostatic device attachable to a hand of a patient, comprising:
  a main body below which first and second inflatable members are attached, wherein
    the first inflatable member is connected to a proximal end of the main body and to be in contact with the hand,
    the second inflatable member is connected to a distal end of the main body and sandwiched between the main body and the first inflatable member, and
    the second inflatable member is located closer to the distal end of the main body than the proximal end thereof;
  a first arm member extending from a first side of the main body that extends between the proximal and distal ends thereof; and
  a second arm member extending from a second side of the main body that extends between the proximal and distal ends thereof,
  wherein the first and second arm members are configured to be wrapped around the hand of the patient and exposed ends of the first and second arm members are attached to each other to secure the main body to the hand of the patient.

12. The hemostatic device according to claim 11, wherein the first and second inflatable members are connected via a communication hole through which a fluid passes.

13. The hemostatic device according to claim 12, wherein the communication hole is located closer to the distal end of the main body than the proximal end thereof.

14. The hemostatic device according to claim 12, wherein the communication hole extends along a direction parallel to the distal end of the main body.

15. The hemostatic device according to claim 11, wherein when the first inflatable member is inflated while the hemostatic device is attached to the hand of the patient, the distal and proximal ends of the first inflatable member lift away from the hand of the patient.

16. The hemostatic device according to claim 11, further comprising:
  a third arm member extending from the distal end of the main body and connectable to the first arm.

17. The hemostatic device according to claim 16, wherein the third arm member is detachable from the main body.

18. A method of securing a hemostatic device to a hand of a patient, the hemostatic device including: a covering member to be worn on the hand of the patient, a securing member that secures the covering member to the hand of the patient, an inflatable member connected to the covering member, and a deformable auxiliary member having a smaller outer shape than an outer shape of the inflatable member, wherein
  the covering member includes a main body, a first arm portion protruding from a first side of the main body, and a second arm portion protruding from a second side of the main body, the main body including a first end portion located on a distal side of the main body between the first arm portion and the second arm portion, and a second end portion located on a proximal side of the main body between the first arm portion and the second arm portion,
  the inflatable member is connected to the second end portion of the main body, and
  the auxiliary member is connected to the first end portion of the main body while being interposed between the main body and the inflatable member, the auxiliary member being located closer to a distal end of the main body than a proximal end thereof, the method comprising:
  placing the hemostatic device on the hand of the patient so that the main body is located at a site where bleeding is to be stopped on the hand of the patient;
  securing the hemostatic device to the hand by connecting the first arm portion to the second arm portion; and
  connecting a syringe to a tube connected to the inflatable member and injecting a fluid into the inflatable member using the syringe to inflate the inflatable member and the auxiliary member.

19. The method according to claim 18, wherein the placing includes aligning a marker of the main body to the site.

20. The method according to claim 18, wherein the auxiliary member is inflated when the fluid injected into the inflatable member forces fluid into the auxiliary member through a communication hole between the inflatable member and the auxiliary member.

* * * * *